US008211436B2

(12) United States Patent
Finn et al.

(10) Patent No.: US 8,211,436 B2
(45) Date of Patent: Jul. 3, 2012

(54) ANTICANCER VACCINE AND DIAGNOSTIC METHODS AND REAGENTS

(75) Inventors: Olivera J. Finn, Pittsburgh, PA (US); Henry Kao, St. Louis, MO (US); Donald F. Hunt, Charlottesville, VA (US); Jarrod A. Marto, Charlottesville, VA (US)

(73) Assignees: University of Pittsburgh—Of the Commonwealth System of Higher Education, Pittsburgh, PA (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/698,822

(22) Filed: Feb. 2, 2010

(65) Prior Publication Data

US 2010/0297158 A1    Nov. 25, 2010

Related U.S. Application Data

(62) Division of application No. 11/366,196, filed on Mar. 2, 2006, now Pat. No. 7,704,507, which is a division of application No. 10/253,867, filed on Sep. 24, 2002, now abandoned.

(60) Provisional application No. 60/324,450, filed on Sep. 24, 2001.

(51) Int. Cl.
*A61K 39/00* (2006.01)
*A61K 35/12* (2006.01)

(52) U.S. Cl. .................................. 424/184.1; 424/277.1

(58) Field of Classification Search ......................... None
See application file for complete search history.

(56) References Cited

U.S. PATENT DOCUMENTS

| 5,424,398 | A | 6/1995 | Middeldorp et al. |
| 5,543,291 | A | 8/1996 | Keyomarsi et al. |
| 5,788,963 | A | 8/1998 | Murphy et al. |
| 5,846,827 | A | 12/1998 | Celis et al. |
| 5,962,318 | A | 10/1999 | Rooney et al. |
| 5,973,119 | A | 10/1999 | Coats et al. |
| 6,225,443 | B1 | 5/2001 | DeMars et al. |
| 6,805,861 | B2 | 10/2004 | Stauss |
| 7,704,507 | B2 | 4/2010 | Finn et al. |
| 2002/0055627 | A1* | 5/2002 | Rosen et al. ............. 536/23.5 |
| 2002/0090362 | A1 | 7/2002 | Stauss |
| 2002/0150891 | A1 | 10/2002 | Hood et al. |
| 2003/0040617 | A9 | 2/2003 | Rosen et al. |
| 2003/0143647 | A1 | 7/2003 | Finn et al. |
| 2006/0147460 | A1 | 7/2006 | Finn et al. |

FOREIGN PATENT DOCUMENTS

| WO | WO 96/12406 A1 | 5/1996 |
| WO | WO 98/33450 A1 | 8/1998 |
| WO | WO 99/60119 A2 | 11/1999 |
| WO | WO 0055351 | * | 2/2000 |
| WO | WO 00/55351 A1 | 9/2002 |
| WO | WO 03/033520 A2 | 4/2003 |
| WO | WO 2005/113595 A2 | 12/2005 |
| WO | WO 2007/044033 A2 | 4/2007 |
| WO | WO 2010/011994 A2 | 1/2010 |

OTHER PUBLICATIONS

Kao et al J. Exp. Med. vol. 194, p. 1313-1323, Nov. 2001, IDS:CK.*
Aarnoudse et al., "TCR Reconstitution in Jurkat Reporter Cells Facilitates the Identification of Novel Tumor Antigens by CDNA Expression Cloning," *Int. J Cancer*, 99(1): 7-13 (May 1, 2002).
Adams et al., "High Affinity Restricts the Localization and Tumor Penetration of Single-Chain Fv Antibody Molecules," *Cancer Res*, 61(12): 4750-4755 (Jun. 15, 2001).
Altschul et al., "Basic Local Alignment Search Tool," *J Mol Biol*, 215(3): 403-410 (1990).
Avigan et al., "Immune Reconstitution Following High-Dose Chemotherapy With Stem Cell Rescue in Patients With Advanced Breast Cancer," *Bone Marrow Transplant*, 26(2): 169-176 (Jul. 2, 2000).
Badou et al., "Mercuric Chloride-Induced Autoimmunity," *Current Protocols in Immunology*, 3(Supplement 32): 15.15.1-15.15.18 (Aug. 1999).
Barnd et al., "Specific, Major Histocompatibility Complex—Unrestricted Recognition of Tumor-Associated Mucins by Human Cytotoxic T Cells," *Proc Natl Acad Sci U S A*,, 86: 7159-7163 (Sep. 1989).
Barratt-Boyes, "Making the Most of Mucin: A Novel Target for Tumor Immunotherapy," *Cancer Immunology Immunotherapy*, 43(3): 142-151 (1996).
Bensinger et al., "High-Dose Busulfan, Melphalan, Thiotepa and Peripheral Bolld Stem Cell Infusion for the Treatment of Metastatic Breast Cancer," *Bone Marrow Transplant*, 19(12): 1183-1189 (Jun. 2, 1997).
Berard et al., "Cross-Priming of Naïve CD8 T Cells Against Melanoma Antigens Using Dendritic Cells Loaded With Killed Allogeneic Melanoma Cells," *J. Exp. Med.*, 192(11): 1535-1543 (Dec. 4, 2000).
Berkner, "Development of Adenovirus Vectors for the Expression of Heterologous Genes," *Bio Techniques*, 6(7): 616-629 (Jul./Aug. 1988).
Boel et al., "BAGE: a New Gene Encoding an Antigen Recognized on Human Melanomas by Cytolytic T Lymphocytes," *Immunity*, 2: 167-175 (Feb. 1995).
Brenner et al., "Gene Marking to Determine Whether Autologous Marrow Infusion Restores Long-Term Haemopoiesis in Cancer Patients," *Lancet*, 342(8880): 1134-1137 (Nov. 6, 1993). Bubenik, "Tumour MHC Class I Downregulation and Immunotherapy," *Oncol Rep*, 10(6): 2005-2008 (Dec. 2003).
Burchell et al., "A Short Sequence, Within the Amino Acid Tandem Repeat of a Cancer-Associated Mucin, Contains Immunodominant Epitopes," *Int J Cancer*, 44(4): 691-696 (Oct. 15, 1989).

(Continued)

*Primary Examiner* — Lei Yao
(74) *Attorney, Agent, or Firm* — Leydig, Voit & Mayer, Ltd

(57) ABSTRACT

The invention provides a method for vaccinating a patient against a malignancy comprising introducing a protein or peptide comprising of all or an immunogenic fragment of a cyclin protein into the patient. The invention further provides a method of identifying tumor antigens.

2 Claims, 14 Drawing Sheets

OTHER PUBLICATIONS

Callan et al., "Selection of T Cell Receptor Variable Gene-Encoded Amino Acids on the Third Binding Site Loop: A Factor Influencing Variable Chain Selection in a T Cell Response," *Eur J Immunol*, 25(6): 1529-1534 (Jun. 1995).

Chung et al., "Functional Three-Domain Single-Chain T-Cell Receptors," *Proc Natl Acad Sci U S A*, 91: 12654-12658 (Dec. 1994).

Covini et al., "Immune Response to Cyclin B1 in Hepatocellular Carcinoma," *Hepatology*, (PubMed Abstract ID 8985268), 25(1): 75-80 (Jan. 1997).

Crystal et al., "A Phase 1 Study, in Cystic Fibrosis Patients, of the Safety, Toxicity, and Biological Efficacy of a Single Administration of a Replication Deficient, Recombinant Adenovirus Carrying the cDNA of the Normal Cystic Fibrosis Transmembrane Conductance Regulator Gene in the Lung," *Human Gene Ther.*, 6(5): 643-666 (May 1995).

Crystal et al., "Evaluation of Repeat Administration of a Replication Deficient, Recombinant Adenovirus Containing the Normal Cystic Fibrosis Transmembrane Conductance Regulator cDNA to the Airways of Individulas with Cystic Fibrosis," *Human Gene Ther.*, 6(5): 667-703 (May 1995).

Davis et al., "Anti-Idiotype Antibodies Can Induce Long-Term Complete Remissions in Non-Hodgkin's Lymphoma Without Eradicating the Malignant Clone," *Blood*, 92(4): 1184-1190 (Aug. 15, 1998).

Derby et al., "Two Internediate-Avidity Cytotoxic T Lymphocyte Clones With a Disparity Between Functional Avidity and MHC Tetramer Staining," *Int Immunol*, 13(6): 817-824 (Jun. 2001).

Diefenbach et al., Rae1 and H60 Ligands of the NKG2D Receptor Stimulate Tumour Immunity, *Nature*, 413(6852): 165-171 (Sep. 13, 2001).

Disi et al., "HER-2/neu Oncogenic Protein: Issues in Vaccine Development," *Critical Reviews in Immunology*, 18(1&2): 37-45 (1998).

Dong et al., "Prognostic Significance of Cyclin E Overexpression in Laryngela Squamous Cell Carcinomas," *Clinical Cancer Research*, 6(11): 4253-4258 (Nov. 2000).

Dudley et al., "A Phase I Study of Nonmyeloablative Chemotherapy and Adoptive Transfer of Autologous Tumor Antigen-Specific T Lymphocytes in Patients With Metastatic Melanoma," *J. Immunother*, 25(3): 243-251 (May/Jun. 2002).

Dudley et al., "Cancer Regression and Autoimmunity in Patients After Clonal Repopulation with Antitumor Lymphocytes," *Science*, 298(5594): 850-854 (Oct. 25, 2002).

Dutta et al., "Cyclins as Markers of Tumor Proliferation: Immunocytochemical Studies in Breast Cancer," *Proc. Natl. Acad. Sci. USA*, 92(12): 5386-5390 (Jun. 6, 1995).

Engel et al., "High-Efficiency Expression and Solubilization of Functional T Cell Antigen Receptor Heterodimers," *Science*, 256(5061): 1318-1321 (May 29, 1992).

Eshhar et al., "The T-Body Approach: Potential for Cancer Immunotherapy," *Springer Semin Immunopathol*, 18(2): 199-209 (1996).

Fernandez et al., "Dendritic Cells Directly Trigger NK Cell Functions: Cross-talk Relevant in Innate Anti-Tumor Immune Responses in Vivo," *Nat Med*, 5(4): 405-411 (Apr. 1999).

Fontenot et al., "Biophysical Characterization of One-, Two-, and Three-Tandem Repeats of Human Mucin (muc-1) Protein Core," *Cancer Research*, 53(22): 5386-5394 (Nov. 15, 1993).

Fontenot et al., "Structure of a Tumor Associated Antigen Containing a Tandemly Repeated Immunodominant Epitope," *Journal of Biomolecular Structure & Dynamics*, 13(2): 245-260 (Oct. 1995).

Freshney, Culture of Animal Cells, A Manual of Basic Technique, (Alan R. Liss, Inc., New York, NY 1983) 4.

Garcia et al., "An $\alpha\beta$ Cell Receptor Structure at 2.5 A and Its Orientation in the TCR-MHC Complex," *Science*, 274(5285): 209-219 (Oct. 11, 1996).

Gaugler et al., "Human Gene MAGE-3 Codes for an Antigen Recognized on a Melanoma by Autologous Cytolytic T Lymphocytes," *The Journal of Experimental Medicine*, 179: 921-930 (Mar. 1994).

Gregoire et al., "Covalent Assembly of a Soluble T Cell Receptor-Peptide-major Histocompatibility Class I Complex," *Natl Acad Sci U S A*, 93(14): 7184-7189 (Jul. 1996).

Gura, "Systems for Identifying New Drugs Are Often Faulty," *Science*, 278: 1041-1042 (1997).

Hanenberg et al., "Colocalization of Retrovirus and Target Cells on Specific Fibronectin Fragments Increases Genetic Transduction of Mammalian Cells," *Nature Medicine*, 2(8): 876-882 (Aug. 1996).

Hassan et al., "Clinical Significance of Cyclin B1 Protein Expression in Squamous Cell Carcinoma of the Tongue," *Clinical Cancer Research*, 7: 2458-2462 (Aug. 2001).

Herman et al., "A Peptide Encoded by the Human MAGE3 Gene and Presented by HLA-B44 Induces Cytolytic T Lymphocytes That Recognize Tumor Cells Expressing MAGE3," *Immunogenetics*, 43(6): 377-383 (1996).

Holmberg et al., "High-Dose Busulfan, Melphalan and Thiotepa Followed by Autologous Peripheral Blood Stem Cell (PBSC) Rescue in Patients With Advanced Stage III/IV Ovarian Cancer," *Bone Marrow Transplant*, 22(7): 651-659 (Oct. 1, 1998).

Holmberg et al., "Clinical Outcome of Breast and Ovarian Cancer Patients Treated With High-Dose Chemotherapy, Autologous Stem Cell Rescue and THERATOPE STn-KLH Cancer Vaccine," *Bone Marrow Transplant*, 25(12): 1233-1241 (Jun. 2, 2000).

Jaffe et al., "Adenoviral Mediated Transfer and Expression of a Normal Human $\alpha$1-Antitrypsin cDNA in Primary Rat Hepatocytes," *Clinical Research*, 39(2): 302A (1991).

Jemal et al., "Cancer Statistics, 2003," *CA Cancer J Clin*, 53(1): 5-26 (Jan./Feb. 2003).

Jones et al., "Improved Methods for Building Protein Models in Electron Density Maps and the Locations of Errors in These Models." *Acta Crystallographica*, A47, (Pt 2): 110-119 (Mar. 1, 1991).

Kao et al., "Identification of Cyclin B1 as an Epithelial Tumor Antigen," *FASEB Journal*, (Abstract 949.6) 15(5): A1206 (Mar. 8, 2001).

Kao et al., "A New Strategy for Tumor Antigen Discovery Based on in Vitro Priming of Naïve T Cells with Dendritic Cells," *Clinical Cancer Research*, 7(3 Supplement): 773s-780s (Mar. 2001).

Kao et al., "Identification of Cyclin B1 as a Shared Human Epithelial Tumor-Associated Antigen Recognized by T Cells," *J. Exp. Med.* 194(9): 1313-1323 (Nov. 5, 2001).

Kawamoto et al., "Expression of the G2-M Checkpoint Regulators Cyclin B1 and cdc2 in Nonmalignant and Malignant Human Breast Lesions," *The American Journal of Pathology*, 150(1): 15-23 (Jan. 1997).

Kiessling et al., "Immunosuppression in Human Tumor-Host Interaction: Role of Cytokines and Alterations in Signal-Transducing Molecules," *Springer Seminars in Immunopathology*, 18(2): 227-242 (1996).

Kim et al., "Cyclin E Overexpression as an Independent Risk Factor of Visceral Relapse in Breast Cancer," *European Journal of Surgical Oncology*, 27: 464-471 (2001).

Klug et al., "Inactivation of a GFP Retrovirus Occurs at Multiple levels in Long Term Repopulating Stem Cells and Their Differentiated Progeny," *Blood*, 96(3): 894-901 (Aug. 1, 2000).

Koehne et al., "Phenotype of Lymphocyte Subsets After Autologous Peripheral Blood Stem Cell Transplantation," *Bone Marrow Transplant*, 19(2): 149-156 (Jan. 2, 1997).

Kondo et al., "Biology of Hematopoietic Stem Cells and Progenitors: Implications for Clinical Application," *Annul Review of Immunology*, 21: 759-806 (2003).

Kraulis et al., "MOLSCRIPT: A Program to Produce Both Detailed and Schematic Plots of Protein Structures," *Journal of Applied Crystallography*, 24(1): 946-950 (Feb. 1, 1991).

Kushner et al., "Aberrant Expression of Cyclin A and Cyclin B1 Proteins in Oral Carcinoma," *Journal of Oral Pathology & Medicine*, 28(2): 77-81 (Feb. 1999).

Magarian-Blander et al., "Specific and Effective T-Cell Recognition of Cells Transfected With a Truncated Human Mucin cDNA," *Ann N Y Acad Sci*, 690: 231-243 (1993).

Magarian-Blander et al., "Intercellular and Intracellular Events Following the MHC-Unrestricted TCR Recognition of a Tumor-Specific Peptide Epitope on the Epithelial Antigen MUC1," *Journal of Immunology*, 160(7): 3111-3120 (Apr. 1, 1998).

Medzhitov et al., "Innate Immunity: The Virtues of a Nonclonal System of Recognition," *Cell*, 91(3): 295-298 (Oct. 31, 1997).

Merritt et al., "Raster3D: Photorealistic Molecular Graphics." *Methods in Enzymology*, 277: 505-524 (1997).

Mittelbrunn et al., "Cutting Edge: Dynamic Redistribution of Tetraspanin CD81 at the Central Zone of the Immune Synapse in Both T Lymphocytes and APC," *Journal of Immunology*, 169(12): 6691-6695 (Dec. 15, 2002).

Molloy et al., "Production of Soluble Single-Chain T-Cell Receptor Fragments in *Escherichia coli* trxB Mutants," *Molecular Immunology*, 35(2): 73-81 (Feb. 1998).

Morgan et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens," *Journal of Immunology*, 171(6): 3287-3295.(Sep. 15, 2003).

Musgrove et al., "Cyclins and Breast Cancer," *Journal of Mammary Gland Biology and Neoplasia*, 1(2): 153-162 (1996).

Novotny et al., "A Soluble, Single-Chain T-Cell Receptor Fragment Endowed With Antigen-Combining Properties," *Proc Nati Acad Sci U S A*, 88(19): 8646-8650 (Oct. 1991).

Ohashi et al., "Efficient Transfer and Sustained High Expression of the Human Glucocerebrosidase Gene in Mice and Their Functional Macrophages Following Transplantation of Bone Marrow Transduced by a Retroviral Vector," *Proc Natl Acad Sci U S A*, 89: 11332-11336 (Dec. 1992).

Ostrand-Rosenberg, "Tumor Immunotherapy: The Tumor Cell as an Antigen-Presenting Cell," *Current Opinion of Immunology*, 6(5): 722-727 (1994).

Pavlinkova et al., "Pharmacokinetics and Biodistribution of a Light-Chain-Shuffled CC49 Single-Chain Fv antibody Construct," *Cancer Immunology Immunotherapy*, 49(4-5): 267-275 (2000).

Pearlman et al., "AMBER, A Package of Computer Programs for Applying Molecular Mechanics, Normal Mode Analysis, Molecular Dynamics and Free Energy Calculations to Simulate the Structural and Energetic Properties of Molecules," *Computer Physics Communications*, 91(1-3): 1-41 (Sep. 11, 1995).

Pinthus et al., "Immuno-Gene Therapy of Established Prostate Tumors Using Chimeric Receptor-redirected Human Lymphocytes," *Cancer Research*, 63(10): 2470-2476 (May 15, 2003).

Restifo et al., "Identification of Human Cancers Deficient in Antigen Processing," *Journal of Experimental Medicine*, 177(2): 265-272 (Feb. 1, 1993).

Rosenberg et al., "Treatment of Patients With Metastatic Melanoma With Autologous Tumor-Infiltrating Lymphocytes and Interleukin 2," *Journal of the National Cancer Institute*, 86(15): 1159-1166 (Aug. 3, 1994).

Rosenfeld et al., "In Vivo Transfer of the Human Cystic Fibrosis Gene to the Respiratory Epithelium," *Clinical Research*, 39(2): 311A (1991).

Rosenfeld et al., "Adenovirus-Mediated Transfer of a Recombinant α1-Antitrypsin Gene to the Lung Epithelium in Vivo," *Science*, 252(5004): 431-434 (Apr. 19, 1991).

Rubinstein et al., "Transfer of TCR Genes into Mature T Cells Is Accompanied by the Maintenance of Parental T Cell Avidity," *Journal of Immunology*, 170(3): 1209-1217 (Feb. 1, 2003).

Sadovnikova et al., "Generation of Human Tumor-Reactive Cytotoxic T Cells Against Peptides Presented by Non-Self HLA Class I Molecules," *Eur. J. Immunol,*, 28: 193-200 (1998).

Saio et al., "Tumor-Infiltrating Macrophages Induce Apoptosis in Activated CD8+ T Cells by a Mechanism Requiring Cell Contact and Mediated by Both the Cell-Associated Form of TNF and Nitric Oxide," *Journal of Immunology*, 167(10): 5583-5593 (Nov. 15, 2001).

Sanderson et al., "LacZ Inducible, Antigen/MHC-Specific T Cell Hybrids," *International Immunology*, 6(3): 369-376 (Mar. 1994).

Schafmeister et al., "LeAP," *C.E.A.F., University of California, San Francisco*, 1-191 (1995).

Slamon et al., "Use of Chemotherapy Plus a Monoclonal Antibody Against HER2 for Metastatic Breast Cancer That Overexpresses HER2," *New England Journal of Medicne*, 344(11): 783-792 (Mar. 15, 2001).

Snyder et al., "Molecular Mechanisms and Biological Significance of CTL Avidity," *Current HIV Research*, 1(3): 287-294 (2003).

Soria et al., "Overexpression of Cyclin B1 in Early-Stage Non-Small Cell Lung Cancer and Its Clinical Implication," *Cancer Research*, 60(15): 4000-4004 (Aug. 1, 2000).

Stanislawski et al., "Circumventing Tolerance to a Human MDM2-Derived Tumor Antigen by TCR Gene Transfer," *Nature Immunology*, 2(10): 962-970 (Oct. 2001).

Traversari et al. "A Nonapeptide Encoded by Human Gene MAGE-1 Is Recognized on HLA-A1 by Cytolytic T Lymphocytes Directed Against Tumor Antigen MZ2-E," *The Journal of Experimental Medicine*, 176: 1453-1457 (Nov. 1992).

Van Den Eynde et al., "A New Family of Genes Coding for an Antigen Recognized by Autologous Cytolytic T Lymphocytes on a Human Melanoma," *The Journal of Experimental Medicine*, 182: 689-698 (Sep. 1995).

Van Der Bruggen et al., Autologous Cytolytic T Lymphocytes Recognize a MAGE-1 Nonapeptide on Melanomas Expressing HLA-Cw*1601*, *European Journal of lmmunolgy*, 24(8): 2134-2140 (Sep. 1994).

Van Der Bruggen et al., "A Peptide Encoded by Human Gene MAGE-3 and Presented by HLA-A2 Induces Cytolytic T Lymphocytes That Recognize Tumor Cells Expressing MAGE-3*," *European Journal of Immunology*, 24(10): 3038-3043 (Dec. 1994).

Vlad et al., "Complex Carbohydrates Are Not Removed During Processing of Glycoproteins by Dendritic Cells: Processing of Tumor Antigen MUC1 Glycopeptides for Presentation to major Histocompatibility Complex Class II-Restricted T Cells," *Journal of Experimental Medicine*, 196(11): 1435-1446 (Dec. 2, 2002).

Wang et al., "A T Cell-Independent Antitumor Response in Mice With Bone Marrow Cells Retrovirally Transduced With an Antibody/Fc-γ Chain Chimeric Receptor Gene Recognizing a Human Ovarian Cancer Antigen," *Nat Med*, 4(2): 168-172 (Feb. 1998).

Wang et al., "Human Tumor Antigens fo Cancer Vaccine Development," *Immunological Reviews*, 170: 85-100 (1999).

Weijtens et al., "Functional Balance Between T Cell Chimeric Receptor Density and Tumor Associated Antigen Density: CTL Mediated Cytolysis and Lymphokine Production," *Gene Therapy*, 7(1): 35-42 (Jan. 2000).

Willemsen et al., "Grafting Primary Human T Lymphocytes With Cancer-Specific Chimeric Single Chain and Two Chain TCR," *Gene Therapy*, 7(16): 1369-1377 (Aug. 2000).

Willemsen et al., "Genetic Engineering of T Cell Specificity for Immunotherapy of Cancer," *Human Immunology*, 64(1): 56-68 (2003).

Yang et al., "Antimelanoma Activity of CTL Generated from Peripheral Blood Mononuclear Cells After Stimulation with Autologous Dendritic Cells Pulsed with Melanoma gp100 Peptide G209-2M Is Correlated to TCR Avidity," *Journal of Immunology*, 169(1): 531-539 (Jul. 1, 2002).

Yee et al., "Adoptive T Cell Therapy Using Antigen-Specific CD8+ T Cell Clones for the Treatment of Patients with Metastatic Melanoma: In Vivo Persistence, Migration, and Antitumor Effect of Transferred T Cells," *Proc Natl Acad Sci U S A*, 99(25): 16168-16173 (Dec. 10, 2002).

Yu et al., "Aberrant Cyclin B1 Expression in Human Tumors and Cell Lines," *FASEB Journal, (Abstract 949.5)* 15(5): A1206 (Mar. 2001).

Yu et al., "Immune Recognition of Cyclin B1 as a Tumor Antigen is a Result of its Overexpression in Human Tumors That is Caused by Non-Functional p53," *Molecular Immunology*, 38(12-13): 981-987 (May 2002).

Supplementary Partial European Search Report dated Aug. 22, 2005, in 02797036.7.

U.S. Appl. No. 11/295,767, filed Dec. 7, 2005.

Attword, *Science*, 290: 471-473 (Oct. 20, 2000).

Blake et al., *The Journal of Experimental Medicine*, 184(1): 121-130 (Jul. 1, 1996).

Brichard et al., *The Journal of Experimental Medicine*, 178(2): 489-495 (Aug. 1, 1993).

Burgess et al., *The Journal of Cell Biology*, 111: 2129-2138 (Nov. 1990).

Chen et al., *Proc. Natl. Acad. Sci. USA*, 94(5): 1914-1918 (Mar. 4, 1997).

Clauser et al., *Analytical Chemistry*, 71(14): 2871-2882 (Jul. 15, 1999).

Coulie et al., *The Journal of Experimental Medicine*, 180(1): 35-42 (Jul. 1, 1994).

De Boer et al., *Blood*, 86(7): 2715-2723 (Oct. 1, 1995).

Eng et al., *Journal of the American Society for Mass Spectrometry*, 5(11): 976-989 (Nov. 1994).
Finn et al., *Immunological Reviews*, 145: 61-89 (1995).
Fisk et al., *The Journal of Experimental Medicine*, 181(6): 2109-2117 (Jun. 1995).
Groner et al., *European Journal of Cancer*, 33: S20 (Jun. 1997).
Henderson at al., *Advances in Immunology*, 62: 217-256 (1996).
Herr et al., *Journal of Immunological Methods*, 191(2): 131-142 (1996).
Hiltbold et al., *Cellular Immunology*, 194(2): 143-149 (Jun. 15, 1999).
Hunt et al., *Science*, 255(5049): 1261-1263 (Mar. 6, 1992).
Hunt et al., *Science*, 256(5065): 1817-1820 (Jun. 26, 1992).
Ikeda et al., *Immunity*, 6: 199-208 (Feb. 1997).
Jerome et al., *Cancer Research*, 51(11): 2908-2916 (Jun. 1, 1991).
Kawakami et al., *Proc. Natl. Acad. Sci. USA*, 91(14): 6458-6462 (Jul. 5, 1994).
Kawakami et al., *The Journal of Immunology*, 154(8): 3961-3968 (Apr. 15, 1995).
Keyomarsi et al., *Proc. Natl. Acad. Sci. USA*, 90(3): 1112-1116 (Feb. 1, 1993).
King et al., *Cell*, 79: 563-571 (Nov. 18, 1994).
Lazar et al., *Molecular and Cellular Biology*, 8(3): 1247-1252 (Mar. 1988).
Lennette et al., *European Journal of Cancer*, 31A(11): 1875-1878 (1995).
Lin et al., *Biochemistry*, 14(8): 1559-1563 (1975).
Magarian-Blander et al., *Glycoconjugate Journal*, 13: 749-756 (1996).
Martin et al., *Analytical Chemistry*, 72(18): 4266-4274 (Sep. 15, 2000).
Mashal et al., *Cancer Research*, 56: 4159-4163 (Sep. 15, 1996).
Murakami et al., *Virchows Arch*, 434: 153-158 (1999).
Murray, *Cell*, 81: 149-152 (Apr. 21, 1995).
Petit et al., *Mammalian Genome*, 10(6): 635-637 (1999).
Ressing et al., *The Journal of Immunology*, 154(11): 5934-5943 (Jun. 1, 1995).
Robbins et al., *The Journal of Experimental Medical*, 183(3): 1185-1192 (Mar. 1, 1996).
Röpke et al., *Proc. Natl. Acad. Sci. USA*, 93(25): 14704-14707 (Dec. 10, 1996).
Schwartz et al., *Proc. Natl. Acad. Sci.*, 84: 6408-6411 (Sep. 1987).
Shubert et al., *Nature*, 404(6779): 770-774 (Apr. 13, 2000).
Shabanowitz et al., *Mass Spectrometry in Biology and Medicine*, (Burlingame et al., eds.), 163-177 (Humana Press, Totowa, N. J., 2000).
Shively et al., *Critical Reviews in Oncology/Hematology*, 2(4): 355-399 (1985).
Skolnick et al., *Trends in Biotech,*, 18: 34-39 (Jan. 2000).
Steeg et al., *Breast Cancer Research and Treatment*, 52: 17-28 (1998).
Tran et al., *Human Pathology*, 29(10): 1085-1090 (Oct. 1998).
Türeci et al., *Molecular Medicine Today*, 3(8): 342-349 (Aug. 1997).
Wang et al., *The Prostate*, 2(1): 89-96 (1981).
Wang et al., *Journal of Cancer Research and Clinical Oncology*, 123(2): 124-127 (1997).
Wang et al., *Science*, 284: 1351-1354 (May 21, 1999).
Wölfel et al., *Science*, 269(5228): 1281-1284 (Sep. 1, 1995).
Yasumura et al., *Cancer Research*, 53: 1461-1468 (Mar. 15, 1993).
Zeh III et al., *Human Immunology*, 39(2): 79-86 (Feb. 1994).
Prosecution history of U.S. Appl. No. 11/295,767, filed Dec. 7, 2005, current as of Feb. 2, 2010.
Prosecution history of U.S. Appl. No. 12/258,545, filed Oct. 27, 2008, current as of Feb. 2, 2010.
U.S. Appl. No. 60/324,450, Finn et al., Sep. 24, 2001.
U.S. Appl. No. 60/634,072, Finn et al., Dec. 7, 2004.
U.S. Appl. No. 61/083,800, Finn et al., Jul. 25, 2008.
Alajez et al., "Therapeutic potential of a tumor-specific, MHC-unrestricted T-cell receptor expressed on effector cells of the innate and the adaptive immune system through bone marrow transduction and immune reconstitution," *Blood*, 105(12): 4583-4589 (Jun. 15, 2005).
Barany et al., "Solid-phase peptide synthesis: a silver anniversary report," *Int. J. Peptide Protein Res.* 30: 705-739 (1987).
Bozzacco et al., "DEC-205 receptor on dendritic cells mediates presentation of HIV gag protein to CD8+ T cells in a spectrum of human MHC I haplotypes," *Proc. Nat. Acad. Sci. USA*, 104(4): 1289-1294 (Jan. 23, 2007).
Fay et al., "Long-term outcomes in patients with metastatic melanoma vaccinated with melanoma peptide-pulsed CD34$^+$ progenitor-derived dendritic cells," *Cancer Immunol. Immunother*, 55: 1209-1218 (2006).
Luckow et al., "Trends in the Development of Baculovirus Expression Vectors," *Bio/Technology*, 6: 47-55 (Jan. 1988).
Lundstrom et al., "Latest development in viral vectors for gene therapy," *Trends in Biotechnology*, 21(3): 117-122 (Mar. 2003).
Maecker et al., "Use of overlapping peptide mixtures as antigens for cytokine flow cytometry," *Journal of Immunological Methods*, 255: 27-40 (2001).
Merrifield, "Solid Phase Peptide Synthesis. I. The Synthesis of a Tetrapeptide," *J. Am. Chem. Soc.*, 85: 2149-2154 (Jul. 20, 1963).
NCBI "Chain B, Crystal Structure of Phospho-Cdk2 in Complex with Cyclin B," Database Entrez-Nucleotide, Accession No. 2JGZ_B (Jun. 20, 2007). Retrieved on Feb. 27, 2010.
NCBI "Cyclin B1 [*Homo sapiens*]," Database Entrez-Nucleotide, Accession No. AAV38930.1 (Oct. 28, 2004). Retrieved on Feb. 27, 2010.
NCBI "*Homo sapiens* cyclin B1 (CCNB1), mRNA," Database Entrez-Nucleotide, Accession No. NM_031966.2 (Jul. 2, 2011). Retrieved on Jul. 7, 2011.
NCBI "Mus musculus cyclin B1 (Ccnb1), mRNA," Database Entrez-Nucleotide, Acciession No. NM_172301.3 (May 15, 2011). Retrieved on Jul. 7, 2011.
NCBI "Unnamed Protein Product [*Homo sapiens*]," Database Entrez-Nucleotide, Accession No. BAF82120.1 (Oct. 28, 2004). Retrieved on Feb. 27, 2010.
Petri et al., "The Crystal Structure of Human Cyclin B," *Cell Cycle*, 6(11): 1342-1349 (Jun. 1, 2007).
Vella, et al., "Healthy individuals have T-cell and antibody responses to the tumor antigen cyclin B1 that when elicited in mice protect from cancer," *PNAS*, 106(33): 14010-14015 (Aug. 18, 2009).
Prosecution history of U.S. Appl. No. 10/253,867, filed Sep. 24, 2002, current as of present.
Prosecution history of U.S. Appl. No. 11/295,767, filed Dec. 7, 2005, current as of present.
Prosecution history of U.S. Appl. No. 11/366,196, filed Mar. 2, 2006, current as of present.
Prosecution history of U.S. Appl. No. 12/258,545, filed Oct. 27, 2008, current as of present.
Prosecution history of U.S. Appl. No. 13/055,907, filed Aug. 8, 2011, current as of present.
European Patent Office, Supplementary Partial European Search Report dated Dec. 12, 2005, in 02797036.7.
European Patent Office, International Search Report dated Aug. 20, 2007, in PCT/US2005/044024.
Korean Intellectual Property Office, International Search Report dated Mar. 5, 2010, in PCT/US09/51853.
United States Patent and Trademark Office, International Search Report dated Oct. 8, 2003, in PCT/US02/30289.
United States Patent and Trademark Office, Office Action dated Apr. 19, 2012, in U.S. Appl. No. 12/258,545.

* cited by examiner

ND DIAGNOSTIC
ANTICANCER VACCINE AND DIAGNOSTIC METHODS AND REAGENTS

CROSS REFERENCE TO RELATED APPLICATIONS

This application is a divisional of U.S. application Ser. No. 11/366,196, filed Mar. 2, 2006 and issued as U.S. Pat. No. 7,704,507, which is a divisional of U.S. application Ser. No. 10/253,867, filed Sep. 24, 2002, now abandoned, which claims priority to U.S. Provisional App. No. 60/324,450, filed Sep. 24, 2001, each of which is incorporated herein by reference.

STATEMENT REGARDING FEDERALLY SPONSORED RESEARCH AND DEVELOPMENT

This invention was made in part with Government support under grant number DAMD 17-97-1-7057 awarded by the United States Department of Defense and grant numbers 2R37 AI33993 and 5PO1CA 73743 awarded by the United States National Institutes of Health. The United States Government has certain rights in the invention.

FIELD OF THE INVENTION

This invention pertains to methods and reagents for diagnosing and vaccinating against cancer.

BACKGROUND OF THE INVENTION

Successful immunotherapy against tumors relies in part on the discovery of tumor-specific antigens that are able to stimulate effective immune responses in the host. Several approaches have been developed over the years for the identification of such tumor-specific antigens. The "genetic approach" uses tumor cDNA libraries transfected into target cells expressing appropriate HLA molecules. The "peptide elution approach" uses peptides eluted from tumor HLA and loaded on target cells bearing the same HLA molecules. The "reverse immunology approach" uses peptide sequences derived from already known oncogenes or other putative tumor associated genes that contain desired HLA anchor motifs. All these approaches depend on the availability of tumor-specific T from cancer patients cell lines or clones derived from cancer patients used to recognize the new targets. Most recently, the SEREX approach has been used in which tumor cDNA expression libraries are screened with sera from cancer patients. Existing methods of identifying tumor antigens pose several concerns. For example, many such methods rely on T cells from cancer patients or use tumor cells as antigen presenting cells (APCs). However, T cells from cancer patients often are defective, and tumor cells are often poor APCs (Kiessling et al., *Springer Seminars in Immunopathology*, 18, 227-42 (1996); Ostrand-Rosenberg, *Cur. Opin. Immunol.*, 6, 722-27 (1994)).

Existing approaches have led to the identification of a panel of tumor antigens (Wang et al., *Immunol. Rev.* 170, 85-100 (1999)), primarily in melanomas (Boel et al., *Immunity*, 2, 167-75 (1995); Gaugler et al., *J. Exp. Med.*, 179, 921-30 (1994); Herman et al., *Immunogenetics*, 43, 377-83 (1996); Traversari et al., *J. Exp. Med.*, 176, 1453-57 (1992); Van den Eynde et al., *J. Exp. Med.*, 182, 689-98 (1995); van der Bruggen et al., *Eur. J. Immunol.*, 24, 3038-43 (1994); van der Bruggen et al., *Eur. J. Immunol.*, 24, 2134-40 (1994)). Very few tumor-specific antigens have been described in epithelial tumors, the best known being the Her-2/neu derived peptides (Disis et al., *Crit. Rev. Immunol.* 18, 37-45 (1998)) and the core peptides of the MUC-1 tandem repeat (Barratt-Boyes et al., *Cancer Immunology, Immunotherapy*, 43, 142-51 (1996)).

In light of the foregoing, there remains a need for an improved method for discovering tumor antigens and also for additional tumor antigens.

BRIEF SUMMARY OF THE INVENTION

The invention provides a method of priming T cells against tumor antigens comprising by obtaining naïve $CD4^+$ or $CD8^+$ T cells from at least one healthy individual, obtaining at least one protein or peptide from at least one cancerous cell; obtaining antigen presenting cells (APCs), culturing the APCs with the protein(s) or peptide(s), and adding the T cells to the culture of the APCs. The primed T cells can then be employed to identify the antigens or used as prophylaxis or treatment for cancers.

The invention also provides cyclin molecules, and fragments derived from cyclin molecules, as tumor antigens. The invention provides a method for diagnosing a malignant or pre-malignant condition within a patient. The invention also provides a method for vaccinating a patient against malignancies comprising introducing a protein or peptide consisting essentially of all or an immunogenic fragment of a cyclin protein into the patient.

These and other aspects of the invention will become apparent upon reading the following detailed description in conjunction with the accompanying drawings.

DETAILED DESCRIPTION OF THE INVENTION

Figure 1:
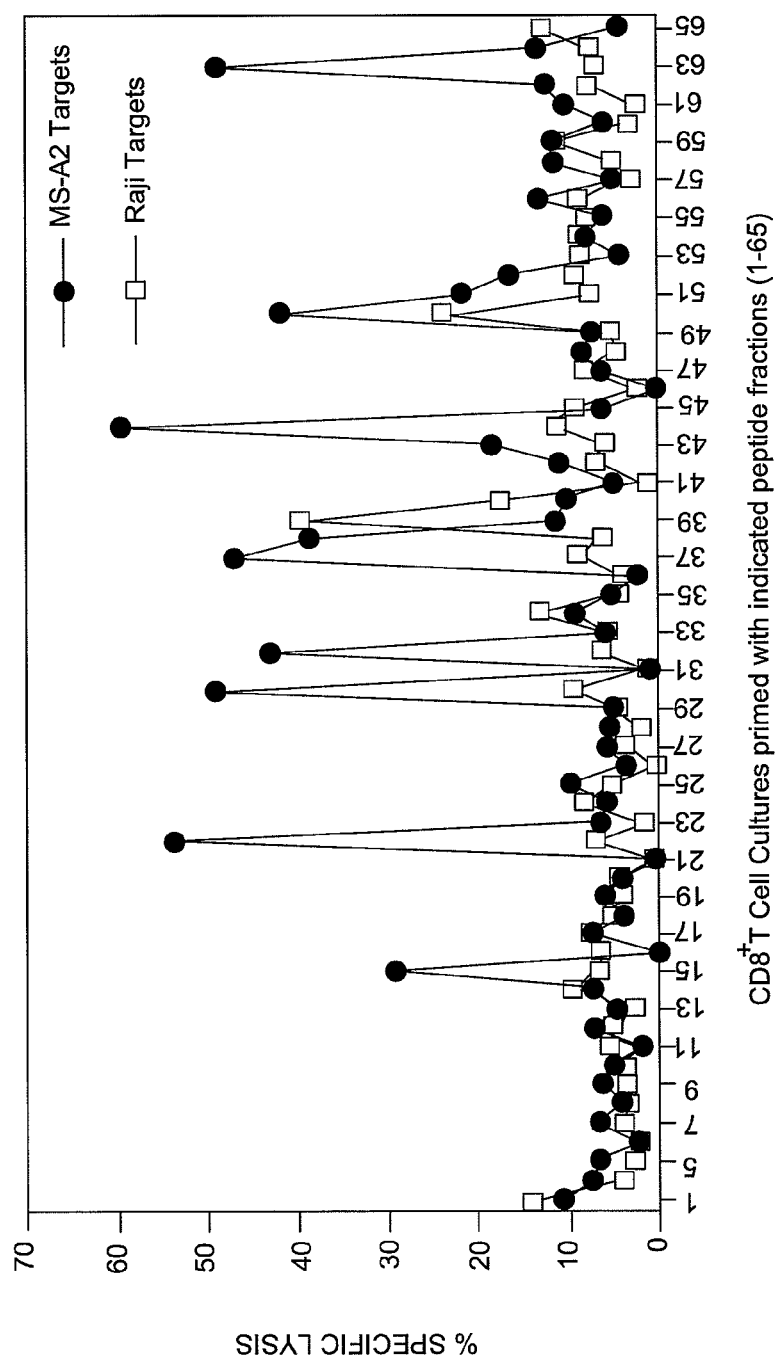
FIG. 1 shows the results of experiments identifying of 12 primed $CD8^+$ T cell cultures that recognized the original tumor, MS-A2, from which the tumor peptides were derived. The primed T cells were tested after the fourth restimulation. E:T ratio was at 100:1. The Raji cell line (A3, B15, C7) was a control for alloreactivity.

In one embodiment, the invention provides a method of priming T cells (e.g., cytotoxic or helper cells) against tumor antigens. The method involves obtaining naïve CD4⁺ or CD8⁺ T cells from at least one healthy individual, obtaining at least one protein or peptide from at least one cancerous cell, and obtaining APCs. The APCs then are cultured with the protein(s) or peptide(s) from the cancer cell(s). Following this period of culturing the APCs with the protein(s) or peptide(s) from the cancer cell(s), the T cells then are added to the culture, and they can be thus cultured for several weeks. Eventually, the T cells become primed against at least one protein(s) or peptide(s) from the cancer cell(s), e.g., they become cytotoxic to or activated by (e.g., to produce cytokines such as IFN-γ) tumor cells (or other cells) expressing or having such protein(s) or peptide(s). Where the method further comprises assessing the peptide sequence of the stimulatory molecules (e.g., the protein(s) or peptide(s)). The method can be used to identify the antigenic protein(s) or peptide(s).

In accordance with the method, naïve CD4⁺ or CD8⁺ T cells are obtained from at least one healthy individual. In this context, "healthy" is taken to indicate an individual who has not been diagnosed with a malignant condition. The naïve CD4⁺ or CD8⁺ T cells can be obtained from such a healthy individual by methods such as are known in the art or as set forth below in the Examples. Of course, using such methods, one of skill in the art is able to obtain a population of CD4⁺ T cells, a population of CD8⁺ T cells, or a mixed population, as desired.

Once the population of CD4⁺ or CD8⁺ T cells is obtained, at least one protein or peptide is obtained from at least one cancerous cell, typically a tumor or cell line containing more than one (and potentially numerous) such cancer cells. While the protein(s) or peptide(s) can be obtained by any suitable method, it is desirable to employ certain methods depending on the type of T cell. In this regard, CD4⁺ T cells typically respond more favorably to larger peptides or mature proteins, whereas CD8⁺ tend to respond more favorably to shorter peptides. Thus, where the T cells are CD4⁺ T cells, the protein(s) or peptide(s) preferably is/are obtained by a method that can extract large peptides or even whole proteins from the cell(s). According to one exemplary method, the cancerous cell(s) can be lysed to obtain a lysate from which the protein(s) or peptide(s) can be extracted. Of course, such extraction can produce a "whole protein" extract, representing all proteins separated from the rest of the lysate. However, if desired, a particular class of protein can be extracted (e.g., by size, gel motility, etc.) from the lysate. Conversely, where the T cells are CD8⁺ T cells, the protein(s) or peptide(s) is/are obtained by a method that can extract smaller peptides from the cell(s). For example, the cancerous cell(s) can be treated to extract HLA class I molecules (which can include type A, B, C, or any allele of HLA class I molecules), which typically are complexed with processed peptides. Such proteins can be obtained from the cell(s) or tumor(s) by methods known in the art (see, e.g., Hunt et al., *Science*, 255, 1261-63 (1992); Henderson et al., *Science*, 255, 1264-66 (1992)). The HLA class 1 molecules then can be treated to release the complexed peptides, which then can be exposed to the CD8⁺ T cells in accordance with the inventive method.

However obtained, the protein(s) or peptide(s) can be fractionated (e.g., using HPLC, and especially RP-HPLC), and even further sub-fractioned as desired, prior to exposure to the CD4⁺ or CD8⁺ T cells. Fractionation (and if desired, sub-fractionation) facilitates identification of the antigen within the fraction of protein(s) or peptide(s), as described herein.

The APCs for use in the inventive method can be any kind of "professional" antigen presenting cell, such as B-cells, dendritic cells, lymphoid fibroblasts, Langerhans cells, macrophages, monocytes, peripheral blood fibrocytes, etc. However, dendritic cells are particularly adept at presenting antigens, and they can be generated in vitro by methods known in the art (see, e.g., Hiltbold et al., *Cancer Res.*, 58: 5066-70 (1998)). As such, preferably, the APCs are dendritic cells. In accordance with the inventive method, the APCs are cultured with the protein(s) or peptide(s) (or fraction or sub-fraction thereof) under conditions suitable for them to present the molecules (e.g., as an MHC I or II presented molecule). For example, with or following exposure to the protein(s) or peptide(s) (or fraction or sub-fraction thereof), the culture of APCs can be maintained in the presence of tumor necrosis factor α.

Following the initial incubation of the APCs with the protein(s) or peptide(s) (or fraction or sub-fraction thereof), the CD4⁺ or CD8⁺ T cells are added to the culture. Typically, the T cells are added to the culture of the APCs in the presence of one or more cytokines (e.g., IL-1b, IL-2, and IL-4, and IL-7), but this is not necessary in all applications. Moreover, the culture can be maintained over several weeks or months, over which period the culture conditions can be maintained or changed, as desired. In this regard, the T cell/APC culture can be restimulated, for example by introducing autologous macrophages, adding or changing the cytokine mixtures, adding additional protein(s) or peptide(s) (or fraction or sub-fraction thereof) or irradiated cancerous cells to the culture. Such cultures can be restimulated several times to enhance the degree to which the T-cells are primed, typically at intervals of from about 5 to about 15 days (e.g., from about 7 to about 10 days). Generally, more restimulation may be desired if the initial protein or peptide concentration is small.

Following this treatment, the CD4$^+$ or CD8$^+$ T-cells can be assayed to determine if they have been primed by any suitable method. For example, cytotoxic T-cells can be cultured with cells from which the protein(s) or peptide(s) (or fraction or sub-fraction thereof) was/were derived (e.g., the same tumor or cell line). The degree to which the T-cells inhibit proliferation of (or even kill) such cells is an indication that the T cells have become primed to be cytotoxic against such cells or tumors.

The primed CD4$^+$ or CD8$^+$ T-cells can be restimulated, such that a stable antigen-reactive T cell culture or T cell line can be maintained for extended periods in vitro. Therefore, T cells reactive to cancer cells can be generated rapidly in large numbers in vitro for various therapeutic and prophylactic applications. The antigen-reactive T cell culture or T cell line can be stored, and used to resupply cytotoxic T cells for long-term use. The primed T cells can be used in vitro, e.g., as part of a diagnostic process for identifying cancers. Alternatively, the primed cytotoxic or helper T cells can be introduced into a patient for prophylaxis or treatment of cancers.

For in vivo use, the invention provides a pharmaceutical composition comprising a therapeutically or prophylactically effective amount of primed T cells and a pharmaceutically acceptable carrier or excipient. Such a carrier includes but is not limited to culture medium with or without serum, buffered saline, dextrose, water, glycerol, ethanol, and combinations thereof. The composition, if desired, also can contain other excipients, such as wetting agents, emulsifying agents, pH buffering agents, and the like. The composition comprising the helper or cytotoxic cells can be introduced into the patients systemically, or locally (e.g., intratumorally). Such a method can be used alone or adjunctively in conjunction with other therapeutic regimens.

In another embodiment, the invention provides cyclin proteins and peptide fragments thereof as antigens, such as tumor antigens, and in particular of epithelial-associated tumors. The cyclin molecule can comprise or consist of a mature cyclin protein, such as cyclin A, D1, B1, or E protein. Alternatively, the molecule can consist essentially of such a protein or an immunogenic peptide fragment thereof. In this regard, an antigenic cyclin peptide can represent a fragment of from about 5 to about 15 contiguous amino acids (e.g., from about 8 to about 12 contiguous amino acids, or even about 9 or 10 contiguous amino acids) of a wild-type human cyclin protein. Such peptides or full length proteins can include some variation from the native sequence, such as having anywhere from 0 to about 5 single amino acid substitutions relative to a wild-type sequence of about 10 amino acids. Exemplary antigenic cyclin-derived peptides are set forth here as SEQ ID NOs: 1-8:

```
SEQ ID NO: 1          AGYLMELCV
SEQ ID NO: 2          AGYLMELCM
SEQ ID NO: 3          AGYLMELCF
SEQ ID NO: 4          AGYLMELCC
```

```
            -continued
SEQ ID NO: 5          AGYLMELCMA
SEQ ID NO: 6          AGYLMELCFA
SEQ ID NO: 7          AKYLMELTM
SEQ ID NO: 8          AKYLMELTML
```

Desirably, the cyclin peptides are able to stimulate (or prime) helper cells or cytotoxic cells (and preferably both types of cells) when presented to them by professional APCs, for example as described above. Such cytotoxic or helper cells can be employed as prophylaxis or treatment of tumors in vivo, such as epithelial tumors (e.g., breast cancer, basal or squamous cell carcinoma, melanoma, cutaneous lymphoma, etc.), particularly those exhibiting deregulated cyclin expression or overexpression of cyclin molecules. For example, activated cytotoxic T cells or helper cells can be introduced into a patient diagnosed with such malignant conditions, either systemically or intratumorally, for example as discussed above or in accordance with methods known in the art (see, e.g., U.S. Pat. No. 6,130,087). Because Cyclin B1 appears to be overexpressed in cells that turn off the function of the tumor suppressor protein p53 (Yu et al., *Mol. Immunol.*, 38(12-13), 981-87 (2002)), patients with p53-negative tumors would be particularly attractive candidates for treatment in accordance with the present invention.

The antigenic protein or peptide can be produced by any suitable method. For example, it can be synthesized using standard direct peptide synthesizing techniques (Bodanszky, Principles of Peptide Synthesis (Springer-Verlag, Heidelberg: 1984)), such as via solid-phase synthesis (see, e.g., Merrifield, *J. Am. Chem. Soc.*, 85, 2149-54 (1963); Barany et al., *Int. J. Peptide Protein Res.*, 30, 705-739 (1987); and U.S. Pat. No. 5,424,398). Alternatively, a gene encoding the desired protein or peptide can be subcloned into an appropriate expression vector using well-known molecular genetic techniques. The protein or peptide can then be produced by a host cell and isolated from the cell. Any appropriate expression vector (see, e.g., Pouwels et al., Cloning Vectors: A Laboratory Manual (Elsevier, N.Y.: 1985)) and corresponding suitable host cells can be employed for production of the desired protein or peptide. Expression hosts include, but are not limited to, bacterial species, mammalian or insect host cell systems including baculovirus systems (see, e.g., Luckow et al., *Bio/Technology*, 6, 47 (1988)), and established cell lines such 293, COS-7, C127, 3T3, CHO, HeLa, BHK, etc. Once isolated, protein or the peptide can be substantially purified by standard methods and formulated into a pharmaceutical composition (e.g., including a pharmacologically- or physiologically-compatible carrier), lyophilized, or otherwise employed or preserved.

Using such cyclin proteins, or peptides derived from cyclin proteins, the invention provides a method for vaccinating a patient against malignancies. The method can be used prophylactically or as a treatment for many types of cancer (e.g., cancers of bladder, bone, brain, breast, cervix, colon, epithelium, esophagus, head and neck, kidney, liver, lung, ovary, pancreas, prostate, skin, stomach, testicle, uterus, etc., and the various leukemias and lymphomas). Because Cyclin B1 appears to be overexpressed in cells that turn off the function of the tumor suppressor protein p53 (Yu et al., *Mol. Immunol.*, 38(12-13), 981-87 (2002)), patients with p53-negative tumors would be particularly attractive candidates for treatment in accordance with the present invention. Moreover, the vaccines can have the potential or capability to prevent cancer in individuals without cancer but who are or may become at risk of developing cancer.

In accordance with this aspect of the invention, a protein or peptide comprising or consisting essentially of all or an immunogenic fragment of a cyclin protein is introduced into a patient under conditions sufficient for the patient to develop an immune response to the protein or peptide. Desirably, the protein or peptide is a Cyclin B1 protein or immunogenic fragment thereof, as set forth herein. The immune response in the patient can help protect the patient against cancers that might develop in the future—i.e., after the vaccination in accordance with the inventive method. For patients diagnosed with cancer, the inventive method can augment the patient's ability to combat the cancer. In this regard, the inventive method can be employed alone or adjunctively with other anticancer treatments (e.g., radiation therapy, chemotherapy, etc.).

The protein or peptide can be introduced into a patient by any desired method. For example, it can be formulated into a pharmaceutical composition including, if desired, a physiologically-compatible buffered solution and injected into the patient (e.g., intradermally, subcutaneously, intramuscularly into the blood stream, or other suitable route). The administration to a patient of a vaccine in accordance with this invention for prophylaxis and/or treatment of cancer can take place before or after a surgical procedure to remove the cancer, before or after a chemotherapeutic procedure for the treatment of cancer, or before or after radiation therapy for the treatment of cancer and any combination thereof. In addition, the vaccine can be given together with adjuvants and/or immuno-modulators to boost the activity of the vaccine and the patient's response.). Moreover, additional inoculations (e.g., "booster" inoculations) can be employed as desired. Following the inoculation(s), the patient's immune response to the antigen can be monitored, for example, by drawing blood from the patient and assessing the presence of immunoglobulins reactive against the cyclin protein or peptide or for the presence of lymphocytes reactive against the protein or peptide.

In another embodiment, the invention provides a method for diagnosing a pre-malignant or malignant condition within a patient. In accordance with one aspect of the method, the patient can be assayed for the expression of a cyclin molecule (e.g., protein or peptide fragment thereof). For example, the method can be employed on biopsied tissue (e.g., lung tissue, lymph nodes, epidermal lesions, breast lesions, dysplastic nevi, colon or cervical polyps, warts, etc.) excised from the patient. The cells of such tissues can be fixed and immunoassayed for the expression of the desired cyclin molecule (e.g., cyclin A, D1, B1, E, etc.). Deregulated cyclin expression supports a diagnosis of a pre-malignant or malignant condition. For example, cytoplasmic staining of Cyclin B1, rather than nuclear staining, is indicative of malignant or pre-malignant cells within the biopsy. Overexpression of the cyclin molecule (e.g., high levels of expression relative to adjacent or control tissue) also can support a diagnosis of a malignant or pre-malignant condition.

In accordance with another aspect of the method, the patient can be assayed for immunoreactivity to cyclin molecules (such as cyclin A, D1, B1, E, etc.). Such reactivity can, for example, be humoral or cellular immunity, which can be assessed by measuring antibody molecules (e.g., immunoglobulins) in fluid (e.g., blood product) drawn from the patient. For example, the titer of anti-cyclin antibodies within the serum of a patient can be ascertained using any standard assay (e.g., ELISA). In other embodiments, immunoreactivity to the cyclin molecule(s) can be assessed by detecting the presence of T cells reactive to the cyclin molecule(s) in fluid or tissue drawn from the patient. The presence of immunoreactivity to the desired cyclin molecule (such as, for example, a noted elevation in the titer of anti-cyclin antibodies in comparison with a standardized baseline or in comparison with healthy patients) can support a diagnosis of a pre-malignant or malignant condition. Such a test can, for example, assist in the diagnosis of lung cancer, prostate cancer, breast cancer, as well as cancers associated with abnormal or absent p53. Of course, the inventive method of diagnosis, however carried out, can be employed alone or in conjunction with other diagnostic methods or in conjunction with the evaluation of other relevant information (such as genetic propensity, family history, identified risk factors, and the like). Thus, for example, the detection of elevated serum anti-cyclin antibody titer in a heavy, long-term smoker (a known risk factor for lung cancers), can serve as an early warning sign of an increase risk in that patient for developing lung cancer. Such a test also can help monitor cancer patients following treatment for the purpose of detecting recurrence, as elevation of anti-cyclin antibody titer correlates with the recurrence of some types of cancers (e.g., lung cancers, adenocarcinoma, etc.).

As discussed above, various aspects of the invention involve treatment of patients and in vivo application of reagents. Such patients typically are mammalian, and can be human. In light of the extensive conservation of the antigen among species, the patient can be selected from any mammalian species (e.g., feline, canine, bovine, porcine, equine, rodent, ungulate, primate, etc.). The patient can be a healthy individual or diseased. In this regard, the methods of prophylaxis can be used to help guard healthy patients from subsequent development of cancers. Methods of treatment can be used to attenuate tumor growth or metastasis, and in some applications such methods can regress tumor growth or reduce tumor size. Indeed, in some applications, the inventive methods, alone or in conjunction with other therapeutic methods, can eliminate tumors or cancerous cells from a patient.

Example 1

This example demonstrates the efficacy of the inventive method of priming T cells (e.g., cytotoxic or helper cells) against tumor antigens.

Materials and Methods

Cell lines. MS (A3, B7, B7, C7, C7; DR15, DQ6 homozygous) is a breast epithelial adenocarcinoma cell line derived from the metastasis of a breast cancer patient. This cell line does not express either MUC-1 or Her-2/neu, the two major epithelial tumor antigens. MS-A2 is the same cell line that was stably transfected with the HLA-A2.1 plasmid (Vega et al., *Proc. Nat. Acad. Sci.*, 86, 2688-92 (1989)) using the calcium phosphate precipitation method (Stratagene, La Jolla, Calif.). The B lymphoma cell line Raji (A3, B15, C7 homozygous; DR3, DR10, DQ1, DQ2) was purchased from the American Type Culture Collection (Manassas, Va.). The chronic myelogenous leukemia cell line K562 was also purchased from ATCC. The melanoma cell line Mel 624 is A2, A3, B7 homozygous. The lung tumor cell line, 201T is A10, A29, B15, B44, also was transfected with the HLA-A2.1 plasmid (designated 201T-A2). Naïve CD4$^+$, CD8$^+$ T cells, dendritic cells, and macrophages were derived from a leukophoresis product of a healthy platelet donor (A2, A29, B7, B44, C7, C7; DR15, DR7, DQ6, DQ2).

Antibodies. Mouse anti-human HLA-DR (L243), CD3 (Leu-4), CD4 (Leu-3a), CD8 (Leu-2a), and CD56 (Leu-19)

were purchased from Becton Dickinson (San Jose, Calif.). Mouse anti-human CD45RO (UCHL1) and CD20 were purchased from DAKO (Carpinteria, Calif.). Goat anti-mouse IgG antibodies were obtained from Zymed Laboratories, Inc. (South San Francisco, Calif.). W6/32, a mouse anti-human MHC Class I antibody, was produced by the W/632 hybridoma obtained from ATCC (Manassas, Va.) and purified via a Protein A-Sepharose column (Sigma, St. Louis, Mo.) in the laboratory.

Isolation of tumor HLA Class I-bound peptides. Preparation of HLA Class I-associated peptides was similar to previously described methods (Hunt et al., *Science,* 255, 1261-63 (1992), Henderson et al., Science, 255, 1264-66 (1992)). MS-A2 tumor cells were grown in 10-chamber cell factories (Nalge Nunc, Naperville, Ill.), and expanded weekly until >1.5×10$^{10}$ cells were obtained. The cells were washed three times in ice-cold PBS, pelleted and stored at −800 C for later use. Detergent lysis buffer (1% CHAPS) and a cocktail of protease inhibitors (2 mM PMSF, 100 mM Iodoacetamide, 5 mg/ml Aprotinin, 10 mg/ml Leupeptin, 10 mg/ml Pepstatin A, 3 ng/ml EDTA, and 0.04% sodium azide) (Sigma, St. Louis, Mo.) were used to solubilize the cells at 4° C. for 1 hr. The cell lysate was spun at 100,000×g for 1 hour to remove insoluble proteins, and the supernatant was filtered through a 0.22 mm filter (Millipore, Bedford, Mass.) to further remove debris from the suspension. The supernatant was then passed through a Protein A-Sepharose anti-class I (W6/32) column (BioRad, Hercules, Calif.) overnight. The column then was washed 30 times sequentially with low salt (150 mM NaCl, 20 mM Tris pH 8.0), high salt (1 M NaCl, 20 mM Tris pH 8.0), and Tris buffer (20 mM Tris pH 8.0). Class I molecules then were eluted from the column using 0.2N acetic acid, and peptides were extracted from the Class I molecules by boiling in 10% acetic acid for 5 minutes. The released peptides were further purified using 5 kD cut-off microconcentrators (Amicon, Bedford, Mass.), vacuum centrifuged to reduce the volume, and frozen at −800° C.

Fractionation of peptide extracts. The peptide extracts were fractionated by reverse phase HPLC on a Rainin HPLC separation system (Varian, Woburn, Mass.). The peptide extracts were concentrated to 150 ml via vacuum centrifugation, and injected into a Brownlee Aquapore (Applied Systems Inc., San Jose, Calif.) C18 column (column dimensions: 2.1 mm×3 cm, pore size: 300 Å, particle size: 7 mm) on the HPLC. The peptides were eluted with a 65 minute trifluoracetic acid/acetonitrile gradient [v/v 0-15% for 5 minutes, 15-60% for 50 minutes, and 60-100% for 10 minutes solvent B (60% acetonitrile in 0.085% TFA) in solvent A (De-ionized water in 0.1% TFA) with a flow rate of 200 ml/min]. Two hundred microliter fractions were collected at one minute intervals, concentrated via vacuum centrifugation to 40 ml, and divided into 4 aliquots, 3 for the use in T cell stimulation and 1 for mass spectrometry analysis.

Fractionation of protein extracts. >1×10$^9$ MS tumor cells were lysed in detergent buffer, spun at 100,000×g, and then filtered using a 0.22 mm filter as above. The supernatant was dialyzed overnight in Tris Buffered Saline pH 7.2 (TBS) (Sigma) to remove detergent. The protein extract was concentrated by vacuum centrifugation, and one-tenth of the extract (~1×10$^8$ cell equivalents) was fractionated by reverse-phase HPLC using a Phenomenex Jupiter C4 column (column dimensions: 4.6 mm×150 mm, pore size: 300 Å, particle size: 7 mm) (Torrence, Calif.). The proteins were eluted with a 60 minute TFA/acetonitrile gradient (10-80% acetonitrile in 60 minutes) at a flow rate of 500 ml/min. Five hundred microliter fractions were collected at one minute intervals, concentrated by vacuum centrifugation to 100 ml, and divided into 4 aliquots each for later use. All solvents were HPLC grade and were obtained from VWR Scientific Products (West Chester, Pa.).

Sub-Fractionation of protein fractions. 25% of a specific protein fraction obtained from the primary fractionation was further sub-fractionated by reverse-phase HPLC using a Phenomenex Jupiter C4 column (column dimensions: 4.6 mm×150 mm, pore size: 300 Å, particle size: 7 mm) (Torrence, Calif.). The proteins were eluted with a shallow gradient (55-62% acetonitrile in 10 minutes) at a flow rate of 500 ml/min, and fractions were collected at one minute intervals. The sub-fractions were then further concentrated by vacuum centrifugation, with 33% of the material loaded onto a 15% SDS-PAGE gel and visualized using a silver stain analysis kit (BioRad), and 33% was loaded onto macrophages and used in a proliferation assay.

Generation of dendritic cells (DCs) in vitro. DCs were cultured in vitro for 7 days as described previously (Hiltbold et al., *Cancer Res.,* 58, 5066-70 (1998)). PBMCs from a healthy donor were isolated after centrifugation over Lymphocyte Separation Medium (Organon Teknika, Durham, N.C.) and washed extensively with PBS to eliminate residual platelets. The cells were plated in a T-75 flask for two hours in serum-free AIM-V (Life Technologies, Grand Island, N.Y.) medium, after which the non-adherent cells were removed and used as the source of naïve T cells. The adherent cells were treated with 1000 U/ml GM-CSF and 26 ng/ml IL-4 (Schering Plough, Kenilworth, N.J.) for 7 days in serum-free AIM-V (Life Technologies) medium supplemented with 2 mM L-glutamine and penicillin/streptomycin. DCs were fed with additional media and cytokines on Day 4 of culture, and purified on Day 7 by negative selection of contaminating T, B, and NK cells. The cells were stained with anti-CD3, -CD19, and -CD56 antibodies for 45 minutes in cold PBS and washed in PBS supplemented with 5% human AB serum (Gemini Products, Calabasas, Calif.). Magnetic DYNAL beads (Lake Success, N.Y.) coated with goat anti-mouse IgG were then added to the cells for 45 minutes, and the contaminating cells were removed by magnetic separation. Flow cytometry analysis of the remaining cells showed they were high HLA-DR+ and B7-2+.

Generation of naïve CD8$^+$ and CD4$^+$ T cells. Non-adherent cells obtained after plastic adherence for DC isolation was used as the source of naïve CD8$^+$ or naïve CD4$^+$ T cells. To purify naïve CD8$^+$ T cells, the cells were stained with anti-CD4, -CD20, CD56, and CD45RO antibodies for 45 minutes in cold PBS and washed in PBS with 5% HAB serum. Four 100-mm petri dishes (Nunc LabTek, Naperville, Ill.) were precoated with 10 mg/ml goat anti-mouse IgG antibodies (Zymed) in 0.05 M Tris, pH 9.5 at room temperature for 1 hr and washed with PBS. Cells were added to each plate and incubated at 40° C. for 1 hr. The non-adherent cells collected were the CD45RA+CD8$^+$ T cells. The same procedure was used for purifying naïve CD4$^+$ T cells, except that anti-CD8 antibodies are used instead. All T cell cultures were grown in RPMI medium (ICN, Costa Mesa, Calif.) supplemented with 10% human AB sera (Gemini Products), L-glutamine, and penicillin/streptomycin (Life Technologies).

Priming naïve CD8$^+$ T cells to tumor peptides. To prime naïve CD8$^+$ T cells, 2×10$^4$ dendritic cells were incubated for 2-4 hours first with 25% of each peptide containing RP-HPLC fraction (10 ml), and then overnight in the presence of 1000 U/ml TNF-a (Genzyme, Cambridge, Mass.) in 96-well U-bottom plates (Falcon, Franklin lakes, NJ). 2×10$^5$ autologous naïve CD8$^+$ T cells were added the next day to the DCs in the presence of 2 ng/ml IL-1b (R & D Systems, Minneapolis, Minn.), 20 U/ml IL-2 (DuPont, Wilmington, Del.), and 26 ng/ml IL-4 (Schering Plough). The CD8+ T cell cultures were fed every 3-4 days with 10 U/ml IL-2 and 13 ng/ml IL-4. In addition, 10 ng/ml IL-7 (Pharmingen, San Diego, Calif.) was included in the cytokine mixture after the 2nd restimulation. The CD8+ T cell cultures were restimulated every 7-10 days using autologous macrophages (obtained by plastic adherence) loaded with the individual peptide fractions, until the third restimulation, where autologous macrophages loaded with irradiated (12,000 Rads) MS-A2 tumors (macrophages:tumor=1:5) were used as stimulators (T cells:loaded macrophages=10:1).

Priming naïve CD4+ T cells to tumor proteins. To prime naïve CD4+ T cells, dendritic cells were loaded with 25% of each protein fraction (~25 ml), and treated the same as described for CD8+ T cell priming above. The CD4+ T cell cultures were restimulated every 10-14 days using autologous macrophages loaded with the individual protein fractions (T cells:macrophages=10:1), and fed every 4-5 days with 10 U/ml IL-2 and 13 ng/ml IL-4, depending on growth kinetics. 10 ng/ml IL-7 (Pharmingen) was added to the CD4+ T cell cultures after the second restimulation. For the third restimulation, MS tumor was irradiated for 7 minutes (2.18 J/cm$^2$) using a Spectra Mini II UV-B irradiator (Daavlin, Bryan, Ohio) and loaded onto macrophages overnight (5:1=apoptotic tumor:macrophages) that were used as stimulators (T:loaded macrophages=10:1) the next day.

Cytotoxicity assays. 1-2×10$^6$ target cells were labeled with 50 mCi of Na$_2$$^{51}$CrO$_4$ (Amersham, Arlington Heights, Ill.) for 90 minutes at 37° C. The labeled cells were then washed three times and plated at 1×10$^3$ cells/well in a 96-well V-bottom plate (Costar, Cambridge, Mass.) with various numbers of effector T cells. In addition, a 50-fold excess of unlabeled K562 (5×10$^4$) was added to the wells for 15 minutes prior to the addition of T cells to prevent the detection of lymphokine-activated killer (LAK) activity in the assay. The plates were centrifuged and incubated for 4 hours at 37° C. All determinations were done in triplicate. Supernatants were harvested using a Skatron harvesting press (Skatron Instruments, Sterling, Va.) and counted on a Cobra II series auto gamma counting system (Packard, Meriden, Conn.). Maximum release was obtained by adding 50 ml of 1% Triton X-100 to the labeled target cells. Spontaneous release was obtained by incubating the labeled cells in the absence of T cells. Percent specific lysis was calculated from the following formula: % specific lysis=100×(experimental release−spontaneous release)/(maximum release−spontaneous release). In blocking experiments, anti-MHC Class I Ab (W6/32) was added to the labeled target cells for 30 minutes prior to the addition of the effector T cells.

Proliferation Assays. Autologous macrophages loaded with UV-induced apoptotic MS tumor cells (5:1=apoptotic tumor:macrophages) were seeded in round-bottom 96-well microplates (Costar, Cambridge, Mass.) with primed T cell cultures at a T cell:stimulator ratio of 20:1. For proliferation assays using tumor lysate, MS tumor cell lysate was generated as described previously, and 1.75×10$^8$ cell equivalents were loaded onto 2×10$^6$ autologous macrophages for 2 hours. T cells were added at a T cell:stimulator ratio of 10:1. For the proliferation assay using the sub-fractions of #44, 33% of the sub-fraction was loaded onto 5×10$^4$ macrophages overnight and added to T cells with a T:stimulator ratio of 1:1 the next day. The wells were pulsed with [$^3$H]TdR (Amersham, Life Science) for the last 18 hours of the 5-day period, harvested by a Skatron semiautomatic cell harvester (Skatron Instruments), and counted on a Wallac 1205 beta plate scintillation counter (Gaithersburg, Md.). The results are expressed as mean values of triplicate determinations.

Mass spectrometry analysis. 25% of the RP-HPLC peptide fraction was concentrated by vacuum centrifugation to near dryness and resuspended in 5 ml of 0.1M acetic acid. One microliter of this material was loaded onto a microcapillary C18 column (150 mm×75 mm i.d.), and eluted with a 20 minute linear gradient (v/v 0-80% solvent B (0.1 M acetic acid in 100% acetonitrile) in solvent A (De-ionized water in 0.1 M acetic acid). Flow rates for the nanospray probe (186 nl/min) was achieved by coupling the Rainin HPLC system with an Accurate microflow processor (LC Packings, San Francisco, Calif.) for flow splitting. The nanospray probe was operated at a voltage differential of +3.2 keV. The source temperature was maintained at 300° C. Mass spectra were obtained by scanning from 300-1500 every 3 seconds and summing individual spectra on a Fisons Quattro II triple quadrupole mass spectrometer (Micromass Inc., Loughborough, U.K.).

Results

Identification of HPLC fractions containing immunogenic tumor peptides. CD8+ T cell cultures were primed and restimulated with HPLC fractions as described above. Due to the low amount of peptide, later restimulations were done using macrophages loaded with irradiated MS-A2 tumor cells. Monitoring the CD8+ T cell cultures with an inverted microscope over four restimulations clearly showed that while there was T cell proliferation in all wells, several of the CD8+ T cell cultures were expanding at a much higher rate, suggesting the presence of immunostimulatory peptides in the fractions used for priming in these wells. Most of the unstimulated CD8+ T cell cultures reached senescence after 8 weeks in culture.

FIG. 1 shows the result of one priming experiment in which after the fourth restimulation, all the T cell cultures could be assayed for their ability to recognize the original tumor, MS-A2, from which the peptides were derived. Out of the 65 CD8+ T cell cultures primed on the individual peptide fractions, 12 (Fractions 15, 22, 30, 32, 37, 38, 43, 44, 50, 51, 52, 63) exhibited strong cytotoxicity against the tumor. Since the PBL donor and the tumor were mismatched at the HLA-A3 allele, the Raji tumor cell line (which was matched only at the HLA-A3 allele with the PBL donor) also was used to ensure that the cytotoxic CD8+ T cell cultures were not alloreactive. None of the cultures that killed MS-A2 tumor cells recognized the Raji targets.

Figure 2:
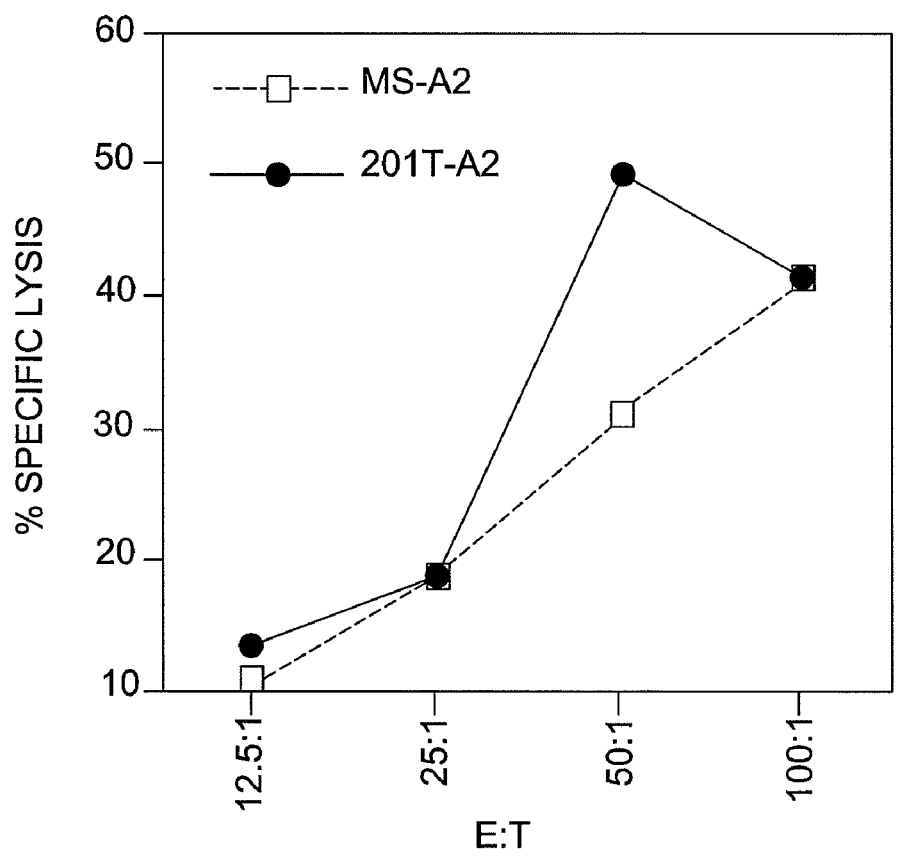
FIG. 2 presents the results of experiments in which $CD8^+$ T cells primed with peptide fraction #32 from MS-A2 tumor recognized a shared tumor antigen on a lung tumor cell line, 201T-A2. $CD8^+$ T cells generated from priming to eluted peptides from Fraction #32 were used in a CTL assay after the fifth restimulation.

The 12 cytotoxic CD8+ T cell cultures also were tested for their ability to recognize another epithelial adenocarcinoma, a lung tumor, 201T-A2, to look for shared tumor antigens. As shown in FIG. 2, a CD8+ T cell culture, primed with peptide fraction #32, recognized again the original tumor, and also the lung tumor. Since the lung tumor and the breast tumor shared only the HLA-A2.1 allele, this suggested that the peptide being recognized was a shared antigen restricted by HLA-A2.1.

Figure 3:
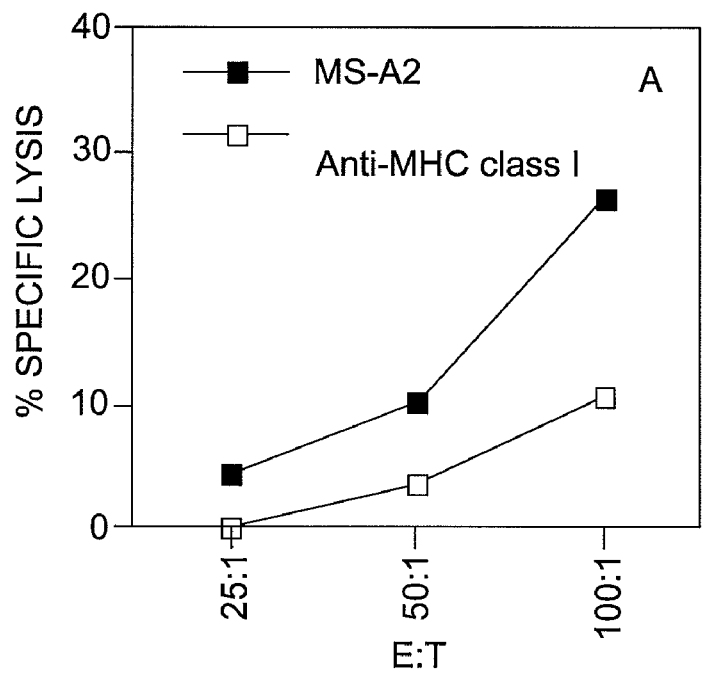
FIG. 3 presents the results of experiments in which $CD8^+$ T cells primed with pooled peptide fractions recognized the original tumor and were HLA Class I-restricted. A) $CD8^+$ T cells primed with peptide fractions #41-46 recognized the original tumor, MS-A2 and were blocked by the anti-MHC Class I antibody, W6/32. B) $CD8^+$ T cells primed with peptide fractions #61-65 recognized the original tumor (MS-A2), and not an HLA-matched tumor, Mel 624.
Figure 3:
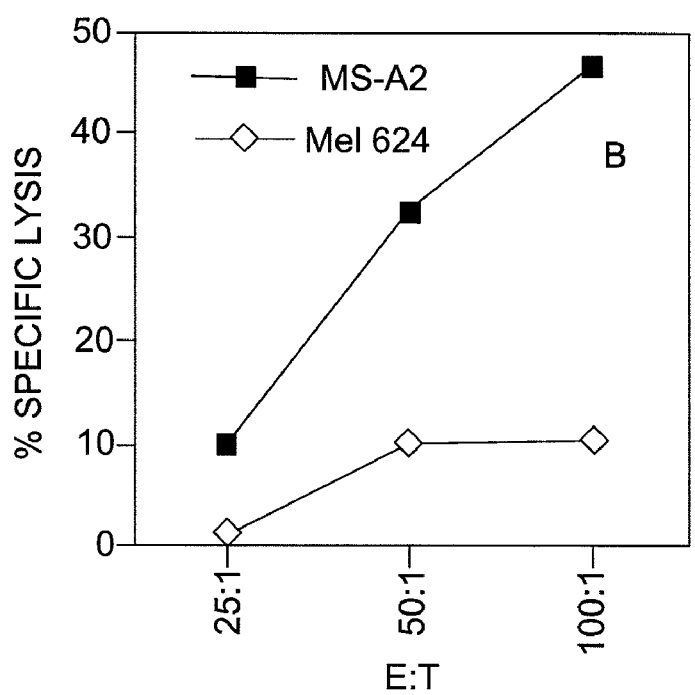

To determine the extent of reproducibility of this approach, the acid extraction was repeated, as was the peptide fractionation and priming procedures. Several consecutive peptide fractions were pooled for two reasons: 1) to compensate for small shifts in fraction number between HPLC runs, and 2) to reduce the total number of T cell cultures in vitro, making the approach less labor intensive. Naive CD8+ T cells were primed on pooled peptide fractions that were composed of the positive peptide fractions identified earlier as well as flanking peptide fractions. The patterns of T cell stimulation and expansion induced by the pooled peptide fractions were consistent with the patterns induced by the immunostimulatory peptide fractions observed in the previous priming. An example is shown in FIG. 3, in which primed CD8+ T cell cultures were primed to fractions 41-46 (FIG. 3A) and 61-65 (FIG. 3B), and generated specificity to the original tumor, MS-A2. This corresponded to immunostimulatory fraction #44 and fraction #63 from the previous run, respectively (FIG. 1). CD8+ T cells primed on fractions 41-46 also were blocked by the MHC Class I antibody, W6/32 (FIG. 3A). Furthermore, the specific antigen was present in the epithelial tumor, and not in the perfectly HLA-matched melanoma, Mel 624 (FIG. 3B).

To evaluate the content of these 12 immunostimulatory fractions, they were analyzed by electrospray ionization nanospray mass spectrometry. A panel of peptide species (Table 1) conforming to mass-to-charge ratios of 700-1300 Daltons indicative of HLA Class I-binding peptides was employed. These results showed that peptides from HLA Class I molecules were extracted, and that there were immunostimulatory peptides in the HPLC fractions that were capable of stimulating naïve CD8+ T cells to proliferate and expand in vitro.

TABLE 1

Mass spectrometry analyses of immunostimulatory peptide fractions[a].

| Fraction # | m/z[b,c] | Fraction # | m/z |
|---|---|---|---|
| 15 | 851.7, 879.8 | 44 | 615.2, 1229.5, 942.3, 921.4, 1061.5 |
| 22 | 921.3, 1061.4 | | |
| 30 | 717 | 50 | 728.1, 949.2, 1256.5 |
| 32 | 717 | 51 | 949 |
| 37 | None | 52 | 949, 885.9 |
| 38 | 921.3 | 63 | 805.6 |
| 43 | 949.2, 816 | | |

[a]HPLC peptide fractions that tested positive in the CTL assay were analyzed by nanospray microcapillary HPLC mass spectrometry.
[b]Mass-to-charge ratio.
[c]Peptide mass to charge ratios (m/z) conforming to peptides that bind HLA Class I molecules (700-1300 Daltons) were considered candidates for tumor antigens.

Identification of HPLC fractions containing immunogenic tumor proteins. CD4+ T cell cultures were primed and restimulated, and by the third restimulation, macrophages loaded with apoptotic MS tumor cells were used to stimulate the CD4+ T cell cultures. Similar to the CD8+ T cell cultures, observation of the CD4+ T cell cultures with an inverted microscope over five restimulations showed that not all the CD4+ T cell cultures were growing equally well, suggesting that the CD4+ T cells were responding to immunostimulatory proteins present in some of these fractions, and not in others. Most of the unstimulated CD4+ T cell cultures reached senescence after 10 weeks in culture.

Figure 4:
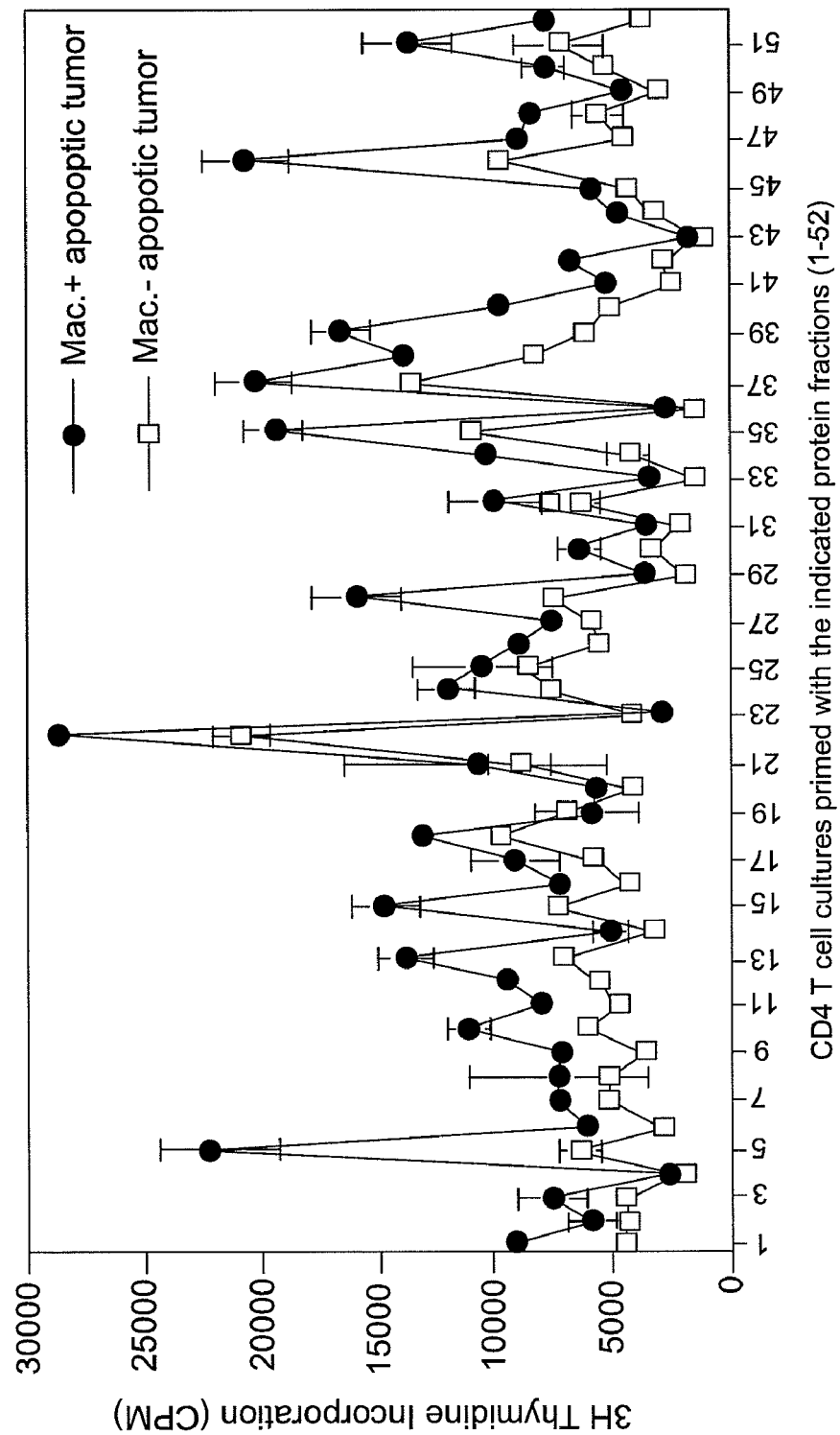
FIG. 4 presents the results of experiments which identified of 12 primed $CD4^+$ T cell cultures that recognized the original tumor, MS, from which the proteins were obtained. The primed $CD4^+$ T cells were tested in a proliferation assay using macrophages loaded with UV-B induced apoptotic tumor (20:1=T:macrophages) after the second restimulation.
Figure 5:
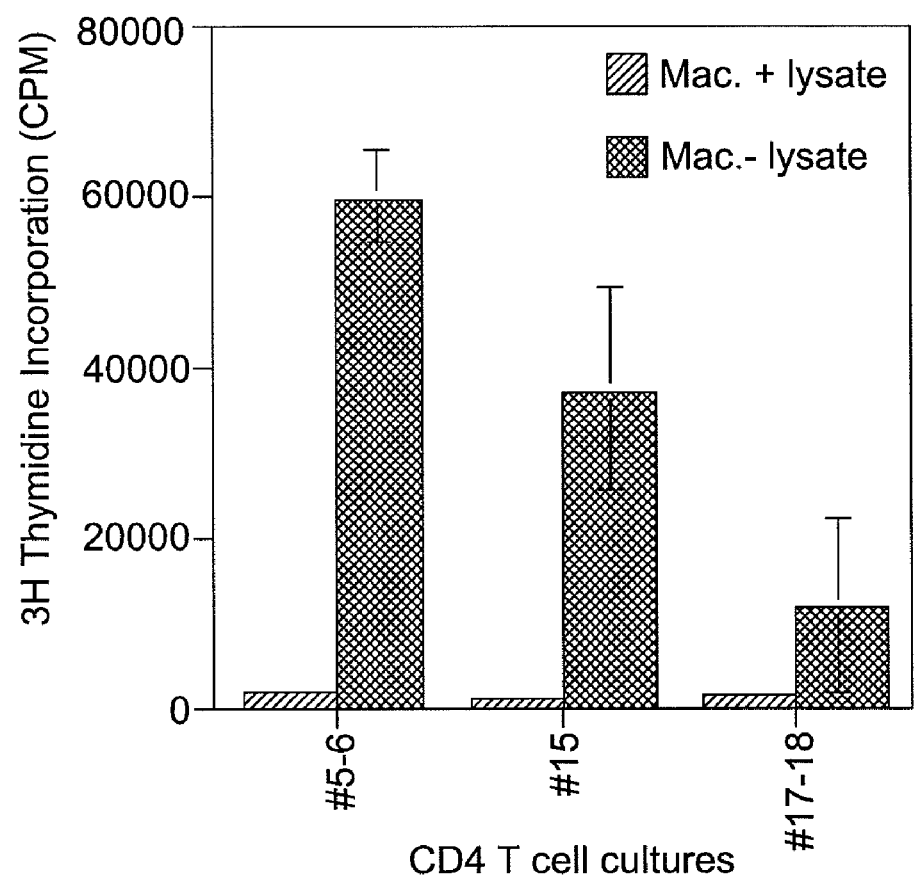
FIG. 5 presents the results of experiments in which $CD4^+$ T cell cultures primed with protein fractions recognize autologous macrophages loaded with tumor lysate. $2 \times 10^6$ autologous macrophages were loaded with $\sim 1.75 \times 10^8$ cell equivalents of tumor lysate for 2 hours and used as stimulators of primed $CD4^+$ T cell cultures in a proliferation assay. T cell cultures were pooled as indicated. T cells were added at a T cell:macrophage ratio of 10:1.

FIG. 4 shows the results of one priming experiment in which after the second restimulation, all the T cell cultures were tested for their ability to recognize the original tumor, MS, from which the proteins were obtained. Autologous macrophages were loaded with apoptotic tumor and used in a 5-day proliferation assay as stimulators of the primed CD4+ T cell cultures. Out of the 52 CD4+ T cell cultures primed on the individual protein fractions, 14 (Fractions 5, 10, 11, 12, 13, 22, 28, 35, 37, 38, 39, 40, 46, 51) proliferated in response to macrophages loaded with apoptotic tumor. The CD4+ T cell cultures also were tested for cytotoxicity against the original tumor via a CTL assay. None of the T cells tested killed the original tumor. Some of the positive CD4+ T cell cultures were also tested for their ability to recognize autologous macrophages loaded with tumor lysate. As shown in FIG. 5, CD4+ T cell cultures primed with protein fractions #5-6 and #15 were able to proliferate to macrophages loaded with tumor lysate, consistent with the results shown in FIG. 4.

Figure 6:
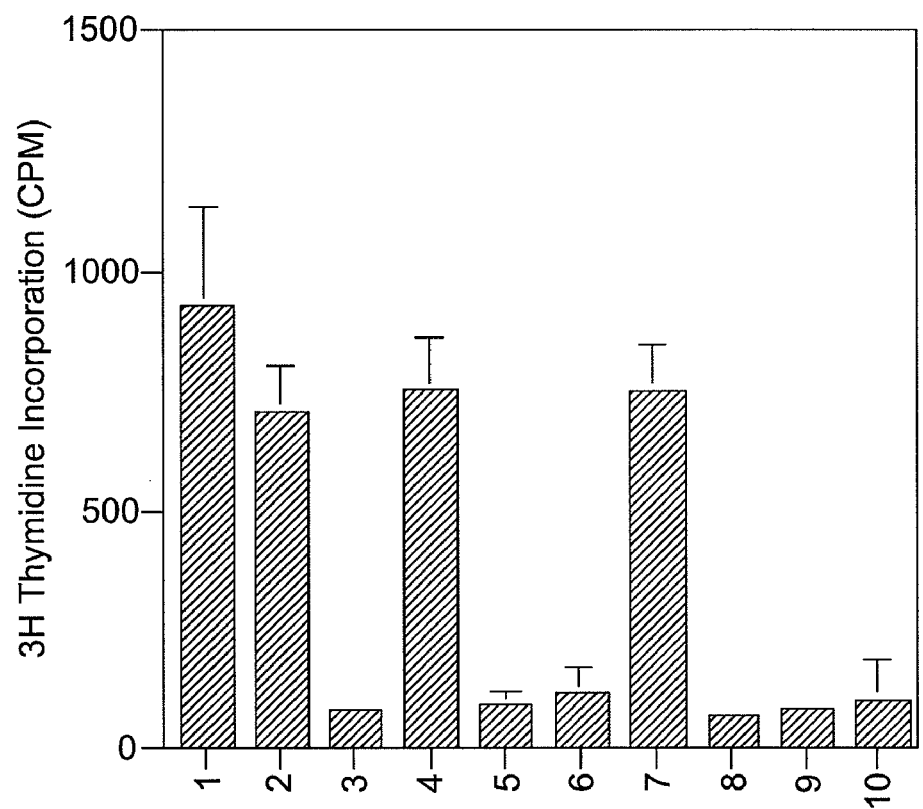
FIG. 6 presents the results of SDS PAGE and functional analysis of subfractions #44.1-#44.10 according to which 33% of each sub-fraction was loaded onto 5×10⁴ macrophages overnight and added to T cells primed to Fraction #44 with a T:stimulator ratio of 1:1 for a 5-day proliferation assay.

To determine the content of the immunostimulatory protein fractions, the protein fractions were analyzed by SDS-PAGE and silver stain analysis. An example is shown in FIG. 6, representing the immunostimulatory protein fraction, Fraction #44, from another priming experiment. This fraction corresponds to Fraction #46 in the first priming experiment (FIG. 4), but it eluted later due to slight variations in HPLC fraction number between runs. Fraction #44 was sub-fractioned into 10 sub-fractions and analyzed for protein content and immunostimulatory capacity. As shown in FIG. 6, immunostimulatory capacity was detected in 4 of the 10 subfractions (#44.1, #44.2, #44.4, and #44.7). A silver stain analysis of the corresponding subfractions detected two bands at 17 & 19 kD in fraction 44.4.

Example 2

This example demonstrates the identification of peptides derived from Cyclin B1 as epithelial tumor associated antigens. It also demonstrates overexpression and deregulated expression of Cyclin B1 in epithelial cancer cells.

Materials and Methods

Cells and Tumor Cell lines. MS-A2 is an HLA-A*0201+ transfected tumor cell line derived from a breast adenocarcinoma cell line, MS (Hiltbold et al., *Cell. Immunol.*, 194, 143-49 (1999)). MS-A2/CD80 is the MS-A2 cell line retrovirally-transduced with the CD80 gene obtained from Corixa Corporation, Seattle, Wash. The lung tumor cell line, 201T, is described above. PCI-13, is a head and neck tumor cell line (Yasumura et al., *Cancer Res.*, 53(6), 1461-68 (1993)). T cells, dendritic cells (DCs), and macrophages were derived from the peripheral blood of HLA-A*0201+ healthy donor and cancer patients under an IRB approved protocol and with signed informed consent.

Peptide Synthesis. All peptides used in this example were synthesized with F-moc chemistry using the 432A Synergy Peptide Synthesizer (Applied Biosystems, Foster City, Calif.). Peptides were purified by RP-HPLC to greater than 85% purity, and dissolved in DMSO and frozen until further use.

Antibodies. MA2.1, a mouse anti-human HLA-A2.1 antibody, was produced by the MA2.1 hybridoma; W6/32, a mouse anti-human MHC Class I antibody, was produced by the W6/32 hybridoma; both were obtained from the American Tissue Culture Collection (ATCC, Manasas, Va.). GNS-1, a mouse anti-human cyclin B1 antibody, was purchased from BD Pharmingen, Franklin Lakes, N.J.

Mass spectrometry (MS) Data Acquisition. Active first-dimension HPLC fractions were screened for peptide content on a home-built Fourier transform mass spectrometer (FTMS), equipped with a nano-flow high performance liquid chromatography micro-electrospray ionization (nano-HPLC micro-ESI) interface (Martin et al., *Anal. Chem.* 72(18), 4266-74 (2000)). Nano-HPLC columns were constructed from 50 mm I.D. fused silica capillaries and packed with an 8 cm bed length of 5 mm diameter reversed phase beads. An integrated microESI emitter tip (~2 mm diameter) was located a few mm from the column bed. Typically, ~0.75 mL (corresponding to ~2.3×10$^8$ cell equivalents or ~1.5%) of an active, first-dimension HPLC fraction was loaded onto a column and eluted directly into the mass spectrometer with a linear, 17 minute gradient of 0-70% acetonitrile in 0.1% acetic acid. Full scan mass spectra, over a mass-to-charge (m/z) range $300 \leq m/z \leq 2500$, were acquired at a rate of approximately 1 scan/second.

Mass Spectrometry/Mass Spectrometry (MS/MS) Data Acquisition. Mass spectrometry/mass spectrometry (MS/

MS) data were acquired on a Finnigan LCQ quadrupole ion trap mass spectrometer (Finnigan Corp., San Jose, Calif.), equipped with a nano-HPLC micro-ESI source as described above. Typically, ~1.5 mL (corresponding to ~4.5×10$^8$ cell equivalents or ~3%) of an active, first-dimension HPLC fraction was loaded onto a column eluted directly into the mass spectrometer with a linear, 30 minute gradient of 0-30% acetonitrile in 0.1% acetic acid. Data dependent spectral acquisition (Shabanowitz et al., "Sequencing the Primordial Soup," pages 163-177 in "Mass Spectrometry in Biology and Medicine" A. L. Burlingame, S. A. Can and M. A. Baldwin, editors. Humana Press (Totowa, N.J. 2000)) was performed as follows: A full scan mass spectrum (MS) was acquired over the range $300 \leq m/z \leq 2000$. The instrument control computer then selected the top 5 most abundant ion species in the MS scan for subsequent MS/MS analysis over the next 5 scans. After acquiring MS/MS data on a particular ion species, its corresponding m/z value was excluded from consideration by the instrument control computer for a period equal to the observed chromatographic peak width (approximately 1.5 minutes for the data herein). This data acquisition procedure minimized redundancy and allowed MS/MS analysis on peptide species whose abundances spanned a wide dynamic range. After acquisition, tandem mass spectral data were searched using SEQUEST (Eng et al., *J. Am. Soc. Mass. Spectrom.* 5, 976-89 (1994)), an algorithm that matches uninterpreted MS/MS spectra to theoretical spectra for peptides generated from user-specified databases. All data were searched against non-redundant (nr) protein databases compiled at the National Center for Biotechnology Information (NCBI). In addition, manual (e.g. de novo) interpretation of MS/MS spectra was performed. Peptide sequence information obtained in this manner was compared to sequences in the nr protein database using the MS-TAG algorithm (Clauser et al., *Anal Chem.*, 71(14), 2871-82 (1999)). Candidate peptide sequences were subsequently confirmed by comparison of their MS/MS spectra acquired for synthetic analogs.

HLA Class I stabilization assays. Peptide-induced stabilization of HLA-A2.1 molecules on T2 cells was done as previously described (Zeh et al., *Hum. Immunol.*, 39(2), 79-86 (1994)). 2×10$^5$ T2 cells were incubated with 20 mg/ml of the indicated synthetic peptides in 3 mg/ml human B2m (Calbiochem, La Jolla, Calif.) for 18-20 hours at room temperature. The cells were then stained with the HLA-A2.1-specific antibody, MA2.1, for 45 minutes, washed with FACS Buffer (PBS, 5% FBS, and 0.01% sodium azide), and stained with a secondary FITC-conjugated anti-IgG antibody (Biosource International, Camarillo, Calif.). The cells were fixed in 4% formaldehyde prior to flow cytometry analysis. The negative control consisted of T2 cells without peptide. The positive control consisted of T2 cells loaded with the Flu matrix peptide, GILGFVFTL (SEQ ID NO:11). Flow cytometric analysis was done using a FACScan flow cytometer (Becton-Dickinson). Experimental results are depicted as X-Fold increase=(Mean Fluorescent Intensity of T2 cells loaded with peptide/ Mean Fluorescent Intensity of T2 cells with no peptide). An X-Fold Increase of >1 indicates that the peptide binds to HLA-A2.1.

IFN-γ ELISPOT Assays. IFN-g ELISPOT assays were conducted as previously described (Herr et al., *J. Immunol. Methods*, 191(2), 131-42 (1996)). Briefly, nitrocellulose plates (Millipore, Bedford, Mass.) were coated with the anti-IFN-γ capture mAb 1-D1K (MabTech, Stockholm, Sweden) overnight at 4° C. For assays using dendritic cells as APCs, DCs were loaded with 10 mg of the indicated peptides for 2-6 hrs, and mixed with autologous T cells at a DC:T ratio of 1:10 for 20 hours at 37° C. For assays using autologous PBMCs as APCs, PBMCs were irradiated at 3000 Rads, loaded with 10 mg of peptides for 4 hours, and mixed with autologous T cells at an APC:T ratio of 1:5 for 40 hours at 37° C. The T cells were seeded at $3 \times 10^3 - 1 \times 10^5$ cells/well. All assays were done in serum-free AIM-V medium (Gibco Life Technologies, Grand Island, N.Y.). The plates were then washed in PBS+0.1% Tween and stained with anti-IFN-γ mAb 7-B6-1 (Mabtech) for 2 hours at 37° C. The plates were washed, and the avidin-peroxidase complex (Vectastain ABC Kit, Vector Laboratories) was added to the plates for 1 hour. The plates were then developed using AEC (Sigma) substrate, and spots were quantified microscopically with an inverted phase-contrast microscope (Carl Zeiss, Hallbergmoos, Germany) along with a computer-assisted image analysis system (KS ELISPOT). For HLA Class I blocking experiments, the W6/32 antibody was added to the APCs for 30-45 minutes prior to the incubation with the T cells.

Priming naïve CD8$^+$ T cells from a healthy donor to cyclin B1 peptides in vitro. Naïve CD8$^+$ T cells and in vitro generated dendritic cells were purified as described above in Example 1. 2×10$^4$ dendritic cells were loaded overnight with 10 mg/well peptide in 96-well U-bottom plates (Falcon, Franklin lakes, NJ) and mixed with 2×10$^5$ autologous naïve CD8$^+$ T cells the next day in the presence of 2 ng/ml IL-1b (R & D Systems, Minneapolis, Minn.), 20 U/ml IL-2 (DuPont, Wilmington, Del.), and 10 U/ml IL-4 (Schering Plough). Depending on growth kinetics, T cells were fed every 3-4 days with 10 U/ml IL-2 and 5 U/ml IL-4. T cells were restimulated every 7-10 days using peptide-loaded autologous macrophages.

Stimulating CD8$^+$ T cells from breast cancer and SCCHN patients with cyclin B1 peptides in vitro. PBMCs from cancer patients were X-irradiated at 3000 Rads, loaded with 10 mg of the indicated peptides for 2-4 hours, and mixed with autologous PBMCs in the presence of 20 U/ml IL-2 (DuPont). The T cell cultures were fed every 3-4 days with 10 U/ml IL-2, and restimulated every 10-12 days, if necessary, using peptide-loaded autologous irradiated PBMCs. All T cell cultures were grown in RPMI medium (ICN, Costa Mesa, Calif.) supplemented with 10% human AB sera (Gemini Products, Calabasas, Calif.), L-glutamine, and penicillin/streptomycin (Life Technologies).

Cytotoxicity assays. 1-2×10$^6$ target cells were labeled with 50 mCi of Na$_2^{51}$CrO$_4$ (Amersham, Arlington Heights, Ill.) for 90 minutes at 37° C. The labeled cells were then washed three times and plated at 1×10$^3$ cells/well in a 96-well V-bottom plate (Costar, Cambridge, Mass.) with various numbers of effector T cells. In addition, a 50-fold excess of unlabeled K562 (5×10$^4$) was added to the wells for 30 minutes prior to the addition of T cells to minimize the detection of lymphokine-activated killer (LAK) activity in the assay. The plates were centrifuged and incubated for 4 hours at 37° C. All determinations were done in triplicate. Supernatants were harvested using a Skatron harvesting press (Skatron Instruments, Sterling, Va.) and counted on a Cobra II series auto gamma counting system (Packard, Meriden, Conn.). Maximum release was obtained by adding 50 ml of 1% Triton X-100 to the labeled target cells. Spontaneous release was obtained by incubating the labeled cells in the absence of T cells. Percent specific lysis was calculated from the following formula: % specific lysis=100×(experimental release−spontaneous release)/(maximum release−spontaneous release).

Immunohistochemical staining of cyclin B1 in tumor cell lines and in tumor sections. For tumor cell lines, the cells were left to adhere overnight on poly-lysine charged slides (Fisher Scientific) in the presence of RPMI+10% FBS (CELLGRO®, Media Tech, Inc., Herndon, Va.). The cells were then fixed for 15 minutes on ice with either 2% Triton-X or 50%

Formalin/50% acetone, blocked with serum, and stained with the anti-cyclin B1 antibody, GNS-1 (BD-Pharmingen). The avidin-biotin peroxidase method was then applied according to manufacturer's instructions using the Vectastain ABC Elite™ staining kit (Vector Laboratories, Burlingame, Calif.). For SCCHN sections, formalin-fixed, paraffin-embedded tumor tissues were sectioned (3-5 mm), air-dried overnight at 37° C., deparaffinized and dehydrated and stained with the anti-human cyclin B1 antibody. The avidin-biotin peroxidase method was applied as above according to the instructions supplied by the manufacturer (DAKO Corporation, Carpinteria, Calif.)

Results

Identification of T cell stimulatory tumor-derived peptides. Peptides were acid-extracted from immunoaffinity purified HLA Class I molecules of an HLA-A*0201 epithelial tumor cell line, fractionated by RP-HPLC, and loaded onto dendritic cells to prime in vitro autologous naïve CD8+ T cells from a healthy donor as described in Example 1. One analyzed RP-HPLC fraction whose peptides supported the growth of tumor-specific CTLs was analyzed by nano-HPLC micro ESI tandem mass spectrometry. Analysis of the resulting MS/MS data yielded 6 candidate peptide sequences that corresponded to the mass range expected for HLA Class I-associated peptides (700-1300 Da). The abundances of these candidates represented the majority of total ion current observed in the mass range of 700-1300 Da. Candidate peptide sequences were subsequently confirmed by comparison of their mass spectra acquired for synthetic analogs. All six peptides had related sequences, with four being 9 amino acids long, and two being 10 amino acids long (Table 2). The four 9-mers (P1-P4) were identical in the first eight amino acids and differed at the C-terminus, where the amino acids were valine (SEQ ID NO:1), methionine (SEQ ID NO:2), phenylalanine (SEQ ID NO:3), and cysteine (SEQ ID NO:4). The two 10-mers, SEQ ID NOs:5 and 6, were identical to SEQ ID NOs 2 and 3, respectively, except for an additional alanine at the C-terminus. When these sequences were entered into the protein database, they were found to be homologous to a human cyclin B1 sequence derived from HeLa cells. These sequences were also homologous to mouse and rat cyclin B1 (Table 2).

TABLE 2

Cyclin B1 sequences derived from the tumor and database bind to HLA-A2.1

| | | Sequence[a] | HLA-A2.1 Binding[b] |
|---|---|---|---|
| Cyclin B1 peptides from the tumor | | | |
| SEQ ID NO:1 (P1) | | AGYLMELCV | 1.60 |
| SEQ ID NO:2 (P2) | | AGYLMELCM | 1.48 |
| SEQ ID NO:3 (P3) | | AGYLMELCF | 1.42 |
| SEQ ID NO:4 (P4) | | AGYLMELCC | 1.61 |
| SEQ ID NO:5 (P5) | | AGYLMELCMA | 1.58 |
| SEQ ID NO:6 (P6) | | AGYLMELCFA | 2.08 |
| Cyclin B1 peptides from the database | | | |
| Human cyclin B1 CB9 | (SEQ ID NO: 7) | AKYLMELTM | 2.28 |
| Human cyclin B1 CB10 | (SEQ ID NO: 8) | AKYLMELTML | 2.25 |
| Mouse cyclin B1 | (SEQ ID NO: 9) | AKYLMELSML | --- |
| Rat cyclin B1 | (SEQ ID NO: 10) | AKYLMELSML | --- |

[a] Tumor-derived peptides were sequenced by electrospray ionization tandem mass spectrometry, yielding six peptides (P1-P6) having high homology to human HeLa cyclin B1 (ascension number: P14635), as well as mouse (ascension number: P24860) and rat cyclin B1 (ascension number: P30277).
[b] X-Fold increase = (Mean Fluorescent Intensity of T2 cells loaded with peptide/Mean Fluorescent Intensity of T2 cells with no peptide). An X-Fold Increase of >1 indicates that the peptide binds to HLA-A2.1. The positive control consisted of T2 cells loaded with the Flu matrix peptide (GILGFVFTL (SEQ ID NO: 11)), which had an X-Fold Increase of 2.2.

Peptides having sequences SEQ ID NOs:1-8 were synthesized and tested for their ability to bind HLA-A2.1 using the T2 cell line and class I stabilization assay. Since leucine and isoleucine have identical masses and are not distinguished by low-energy MS/MS analysis, the peptides were synthesized with leucine at positions 4 and 7 to match leucine present at the same position in the HeLa cyclin B1 sequence, as well as in the mouse and rat cyclin B1 sequences. All the peptides bound to HLA-A2.1, with various affinities, as measured by increases in mean fluorescent intensity in anti-HLA-A2.1 staining of peptide-loaded T2 cells. The HeLa-derived cyclin B1 peptides also bound to HLA-A2.1. Affinities of the HeLa-derived cyclin B1 peptides were higher than that of all tumor-derived peptides, except SEQ ID NO:6 (Table 2).

Figure 7:
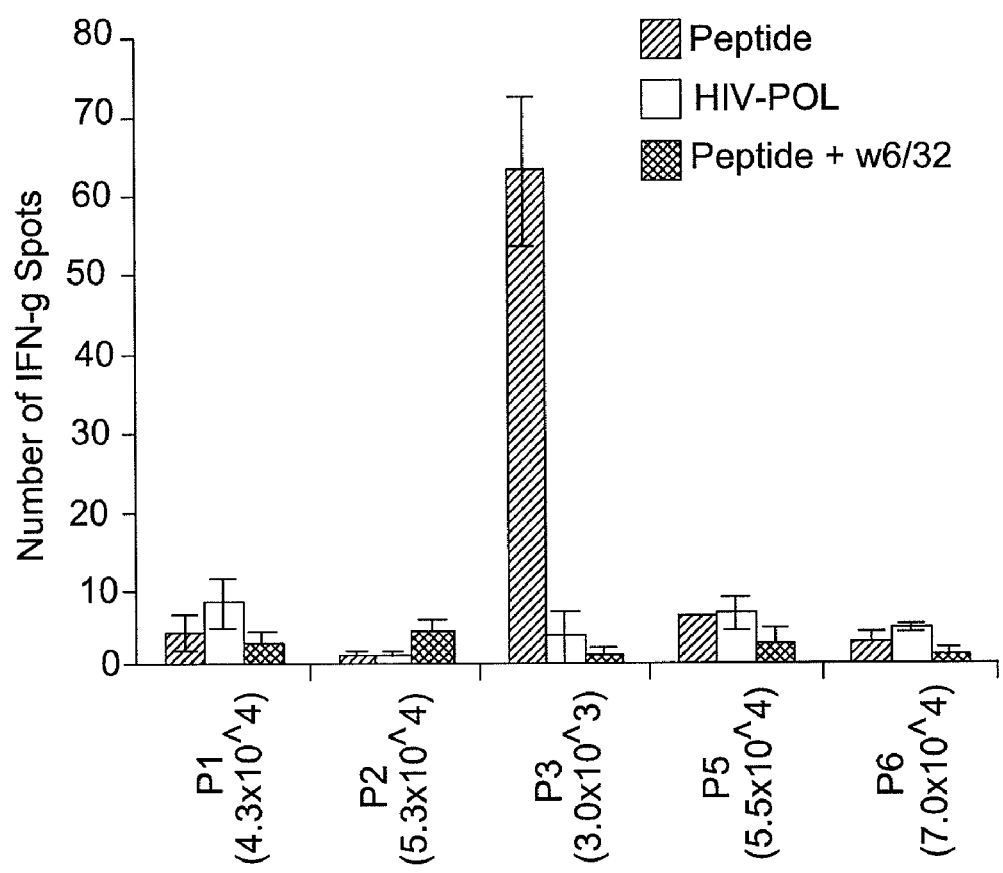
FIG. 7 presents HLA Class I-restricted T cell response of a healthy donor to cyclin B1 peptides. CD8⁺ T cells generated in vitro by priming to synthetic cyclin B1 peptides were used in an IFN-γ assay after the fourth restimulation. Number of T cells per well is indicated in parenthesis.

CD8+ T cells from an HLA-A*0201 healthy donor can be primed to synthetic cyclin B1 peptide SEQ ID NO:4. Since these peptides were derived from a first dimension HPLC fraction that primed tumor-specific CTLs from a HLA-A2.1+ donor, the cyclin B1 peptides were used to prime T cells from another HLA-A2.1+ donor. Naive CD8+ T cells and autologous dendritic cells were loaded with the individual synthetic peptides (SEQ ID NOs:1-6). No T cell responses were detected against the peptides in the absence of in vitro stimulation in this donor as well as another HLA-A2.1+ donor. However, after several rounds of restimulation, antigen-specific IFN-γ secretion by CD8+ T cells in response to SEQ ID NO:4 was detected, but not to other peptides (SEQ ID NOs:1, 2, 5, or 6) or HIV-POL (ILKEPGSHV (SEQ ID NO:12)), which is known to bind HLA-A2.1 and serves here as the negative control (FIG. 7). The T cell response to SEQ ID NO:4 was blocked using the anti-Class I antibody, W6/32, suggesting that the antigen-specific responses were HLA Class I-restricted. However, the T cells that specifically recognized P4-loaded DCs were unable to kill the original tumor from which the peptides were derived. This was not unexpected considering that these T cells were primed with high concentrations of peptide (50 mM), and are thus expected to be of low affinity and incapable of recognizing the comparatively lower levels of the same HLA-peptide complexes on the tumor.

Figure 8:
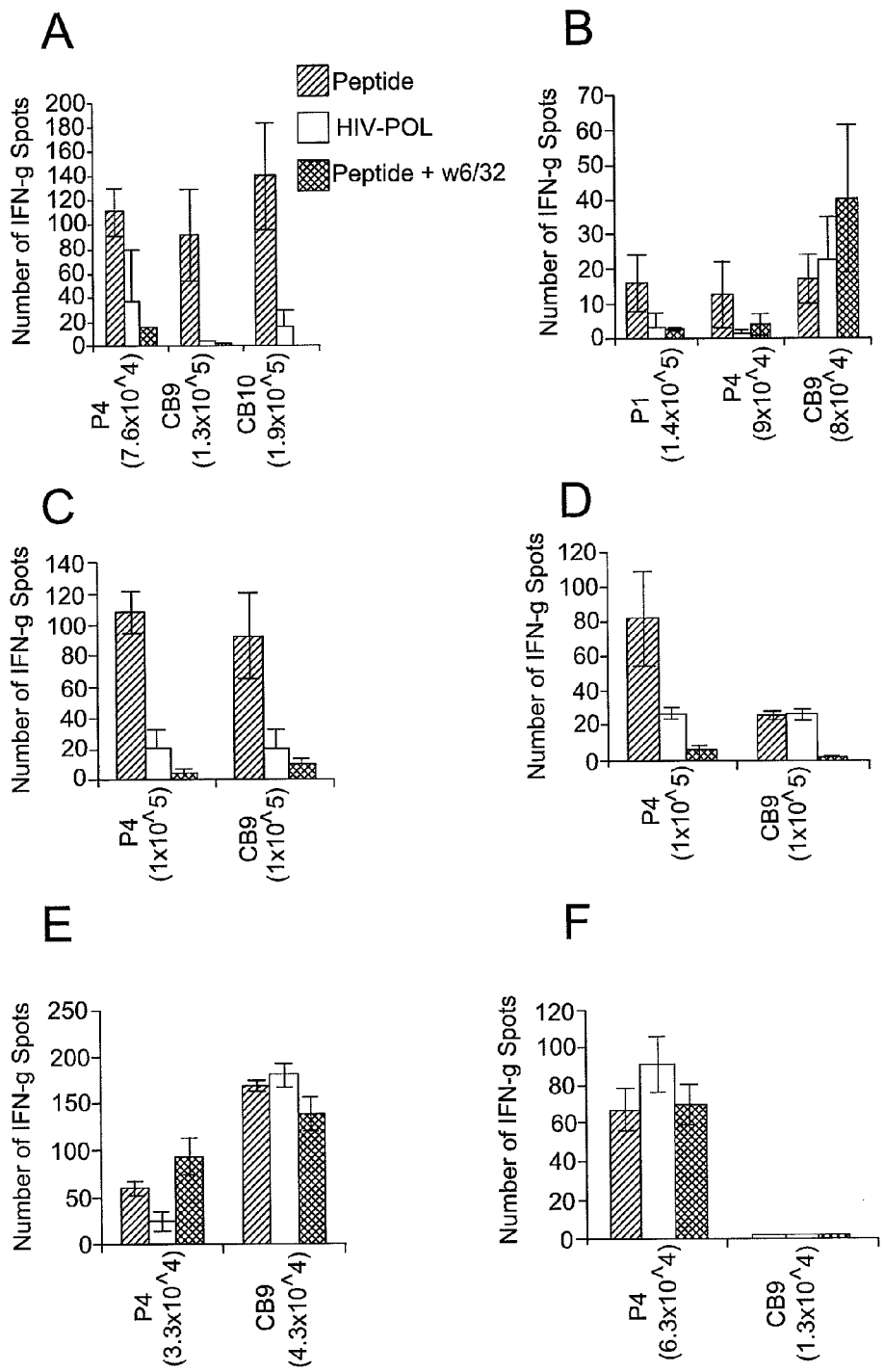
FIG. 8 presents HLA Class I-restricted T cell responses to cyclin B1 peptides in HLA-A2+ breast cancer patients. PBMCs from breast cancer patients were tested for recognition of cyclin B1 peptides after one in vitro stimulation (A, B, E, F) or no in vitro stimulation (C, D) in an IFN-γ assay. Number of T cells per well is indicated in parenthesis.

HLA Class I-restricted memory T cell responses against cyclin B1 peptides in HLA-A*0201 breast cancer patients. PBMCs from six breast cancer patients who had undergone surgery but no chemotherapy were tested for their ability to recognize the cyclin B1 peptides in an IFN-γ ELISPOT assay. Four out of the six HLA-A2+ breast cancer patients tested exhibited secondary responses against one or more of the cyclin B1 peptides (FIG. 8). Patient A exhibited strong HLA Class I-restricted secondary T cell responses to three of the three peptides tested, SEQ ID NOs: 4, 7, and 8, after only one in vitro stimulation. There was no recognition of the HIV-POL control peptide. Patient B appeared to have a weak secondary response to one of the three peptides tested, SEQ ID NO:1, and only after two in vitro stimulations. This patient was later found to be HLA-A*0206, suggesting that, if the response is real, SEQ ID NO:1 may also bind to HLA-A*0206.

Figure 9:
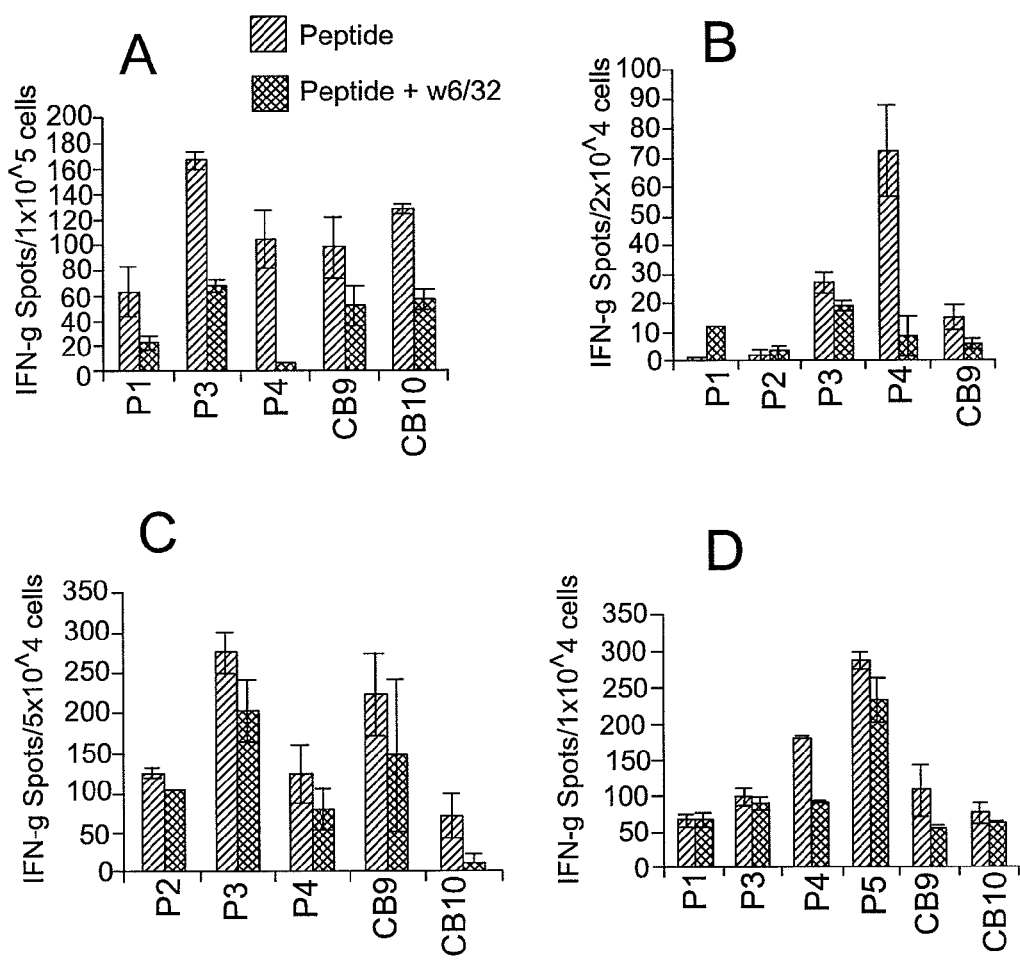
FIG. 9 presents HLA Class I-restricted T cell responses to cyclin B1 peptides in HLA-A2.1+SCCHN patients. PBMCs were tested for recognition of cyclin B1 peptides after one (A) or two in vitro stimulations (B, C, D) in an IFN-γ ELISPOT assay.

Most interestingly, secondary responses were detected in the absence of any in vitro stimulation. Patient C showed peptide-specific HLA Class I-restricted T cell responses to two of two peptides tested, SEQ ID NOs: 4 and 7. Patient D showed strong HLA Class I-restricted T cell responses to P4 and lower responses against both the HIV-POL peptide and SEQ ID NO:7. However, only the SEQ ID NO:7 response was blocked by the anti-MHC Class I antibody, confirming antigen-specificity. Patients E and F did not respond to either of the two peptides tested, SEQ ID NOs: 4 and 7. No response was detected to any peptides in an HLA-A*0201 negative patient HLA Class I-restricted memory T cell responses to cyclin B1 peptides in HLA-A*0201 SCCHN patients. PBMCs from five HLA-A*0201 SCCHN patients for their ability to respond to the cyclin B1 peptides was assessed in an IFN-γ ELISPOT assay. HLA Class I-restricted T cell responses to one or more of the cyclin B1 peptides were detected in four of the five patients tested (FIG. 9). Patient A exhibited HLA Class I-restricted T cell responses to five of eight peptides after only one in vitro stimulation. For two of these peptides, SEQ ID NOs:4 and 7, peptide-specific T cells also were detected in the absence of any in vitro stimulation.

Patient B exhibited HLA Class I-restricted T cell responses to three of the five peptides (SEQ ID NOs: 3, 4, and 7), and not to the other two (SEQ ID NOs:1 and 2). Patient C showed heightened T cell responses to all five peptides tested, but only responses against SEQ ID NOs: 2 and 8 could be blocked with anti-Class I antibody. Patient D had the same heightened T cell response that appeared specific for three of the six peptides tested, SEQ ID NOs: 4, 5, and 7. The fifth SCCHN patient failed to show a detectable response to any of the peptides even after three in vitro stimulations.

Figure 10:
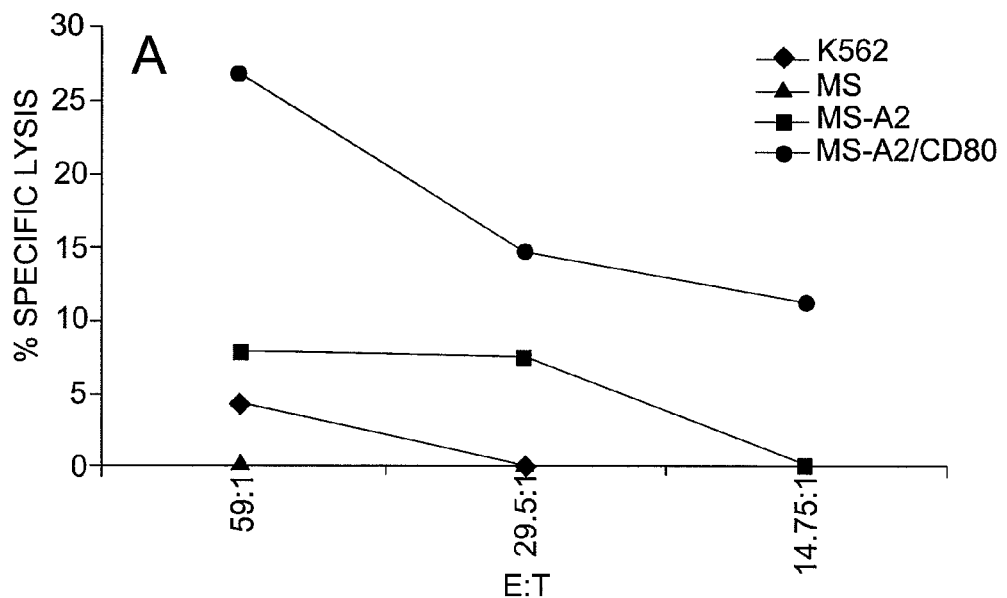
FIG. 10 presents the results of experiments that reveal that T cells from an HLA-A2.1+SCCHN patient restimulated to cyclin B1 peptides in vitro are able to kill the original tumor. T cells restimulated with A) P4, and B) CB9 for 5 days and tested in a CTL assay.
Figure 10:
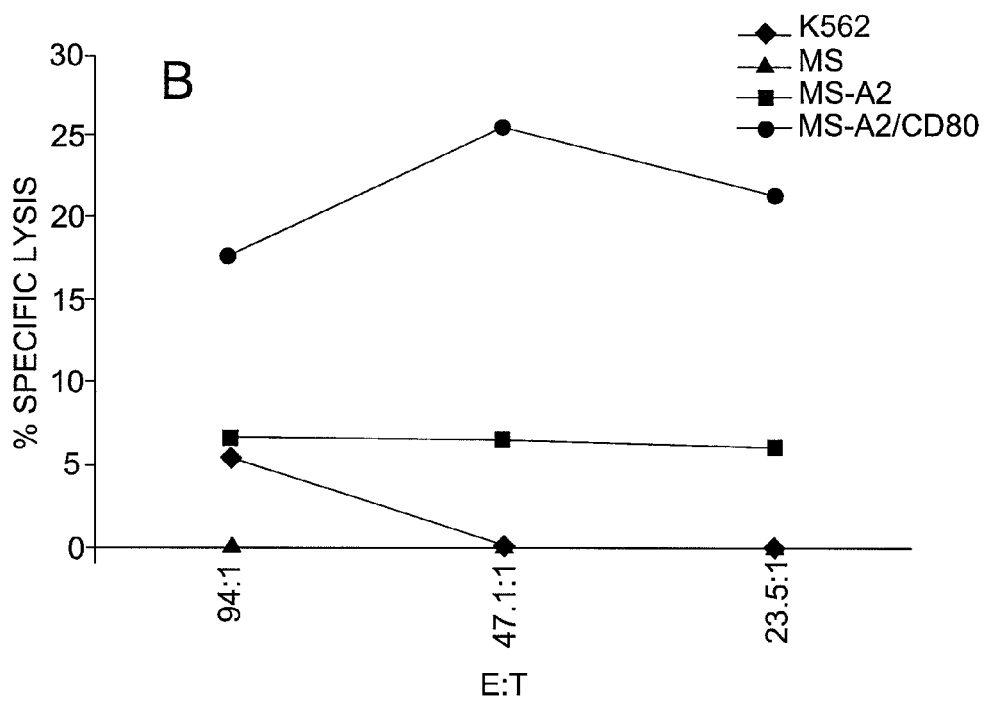

T cells sensitized to SEQ ID NOs: 4 and 7 in one SCCHN patient can lyse the tumor from which the peptides were derived. To determine whether T cells restimulated to cyclin B1 peptides could lyse tumor, T cells from one SCCHN patient (Patient A, FIG. 9) were tested for their ability to kill the original tumor from which the peptides were derived (MS-A2), and the same tumor transduced with the CD80 gene (MS-A2/CD80) to provide "costimulation" for T cell activation. As shown in FIG. 10A, T cells that were sensitized to SEQ ID NO:4 were able to lyse the MS-A2/CD80 tumor and to a lesser extent, MS-A2 tumor, but not the untransfected MS tumor or K562, which is a control for LAK activity. Similarly, in FIG. 10B, T cells sensitized to SEQ ID NO:7 were able to lyse the MS-A2/CD80 tumor and not the other tumors.

Cyclin B1 protein is overexpressed in epithelial tumor cell lines. Cyclin B1 expression was assayed by immunohistochemistry in the original tumor cell line MS-A2 from where they were first isolated and identified. There was intense staining of cyclin B1 protein in the tumor cells, predominantly found in the cytoplasm. Similar intense cytoplasmic staining of cyclin B1 was observed in a human lung adenocarcinoma cell line 201T, also localized in the cytoplasm. No cyclin B1 staining was observed in normal cells, represented by primary cultures of human airway bronchoepithelial cells.

Cyclin B1 protein is overexpressed in SCCHN tumors. To ascertain that the intense staining of cyclin B1 observed in the tumor cell lines was not a result of a prolonged in vitro culture, a tumor cell line and tumor tissue sections obtained from the SCCHN patients whom had been analyzed for cyclin B1-specific T cell responses were examined. Intense cytoplasmic staining of cyclin B1 was observed in the tumor cell line PCI-13, which was derived from a tumor of the SCCHN Patient A described above. Very high expression of cyclin B1 in the cell line correlates with strong cyclin B1-specific T cell responses observed in this patient. Intense cytoplasmic cyclin B1 staining was also observed in the tumor samples of two other patients who exhibited cyclin B1-specific T cell responses (Patients C and D respectively). No cyclin B1 staining was detected in the normal mucosa surrounding the tumor. The tumor showed weak and diffuse cyclin B1 staining that was not convincingly positive. Patient B from whom the tumor was derived did have cyclin B1-specific T cell responses (FIG. 9). The same weak staining was seen in the tumor derived from a patient who did not exhibit any HLA Class I-restricted T cell responses against the cyclin B1 peptides.

Example 3

This Example demonstrates that the presence of Cyclin B1 antibody production correlates with the presence of cancers in patients.

Purified recombinant human cyclin B1 protein was purified from recombinant baculovirus infected insect cells and used it in ELISA assays to screen patients' sera for antibody to Cyclin B1. 7 breast cancer patients were so screened, as were 17 pancreatic cancer patients and 27 colon cancer patients.

Figure 11:
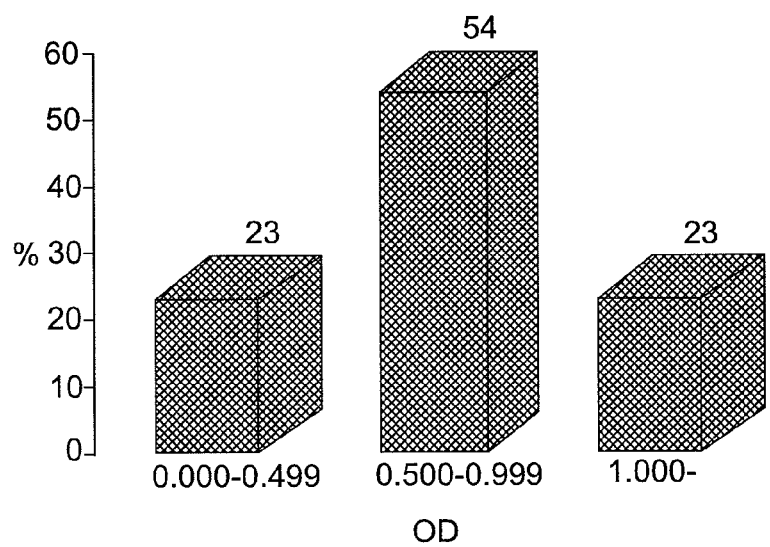
FIG. 11 presents data from experiments revealing the presence of cyclin B1 antibody in the sera of cancer patients.

Of these patients, 23% had close to normal levels (negative) of anti-cyclin B1 antibody. However, 54% of these patients had low to intermediate titers of antibody and 23% had very high titers of antibody (see FIG. 11). In addition, all sera recognized, the purified protein of a correct molecular weight.

Figure 12:
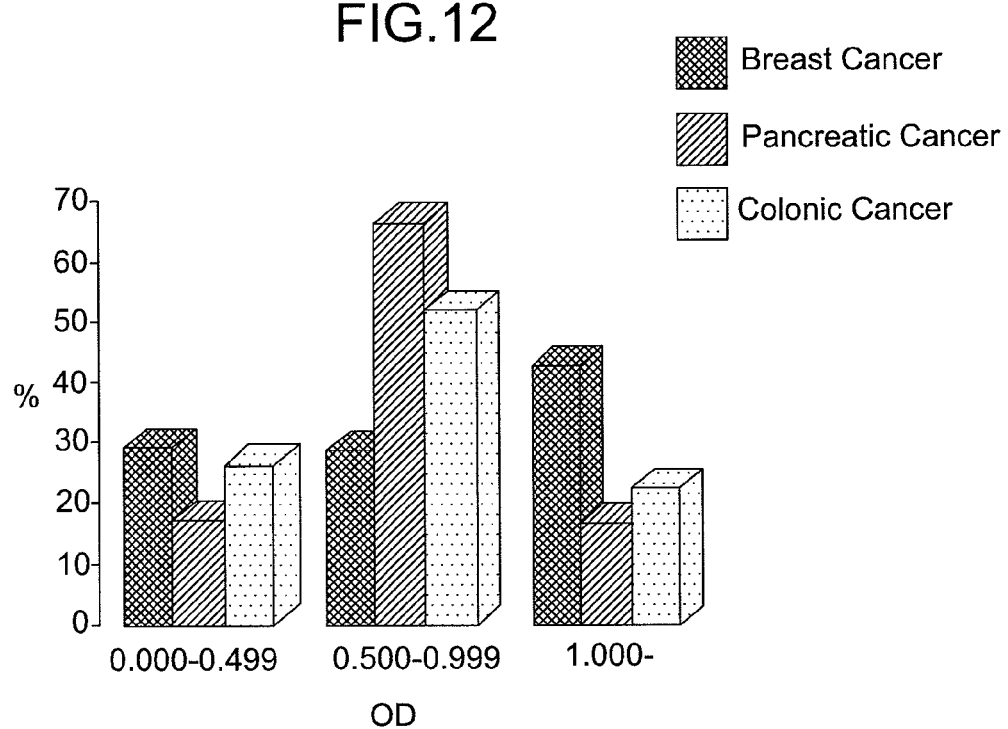
FIG. 12 presents data from experiments revealing the presence of cyclin B1 antibody in the sera of cancer patients.
Figure 13:
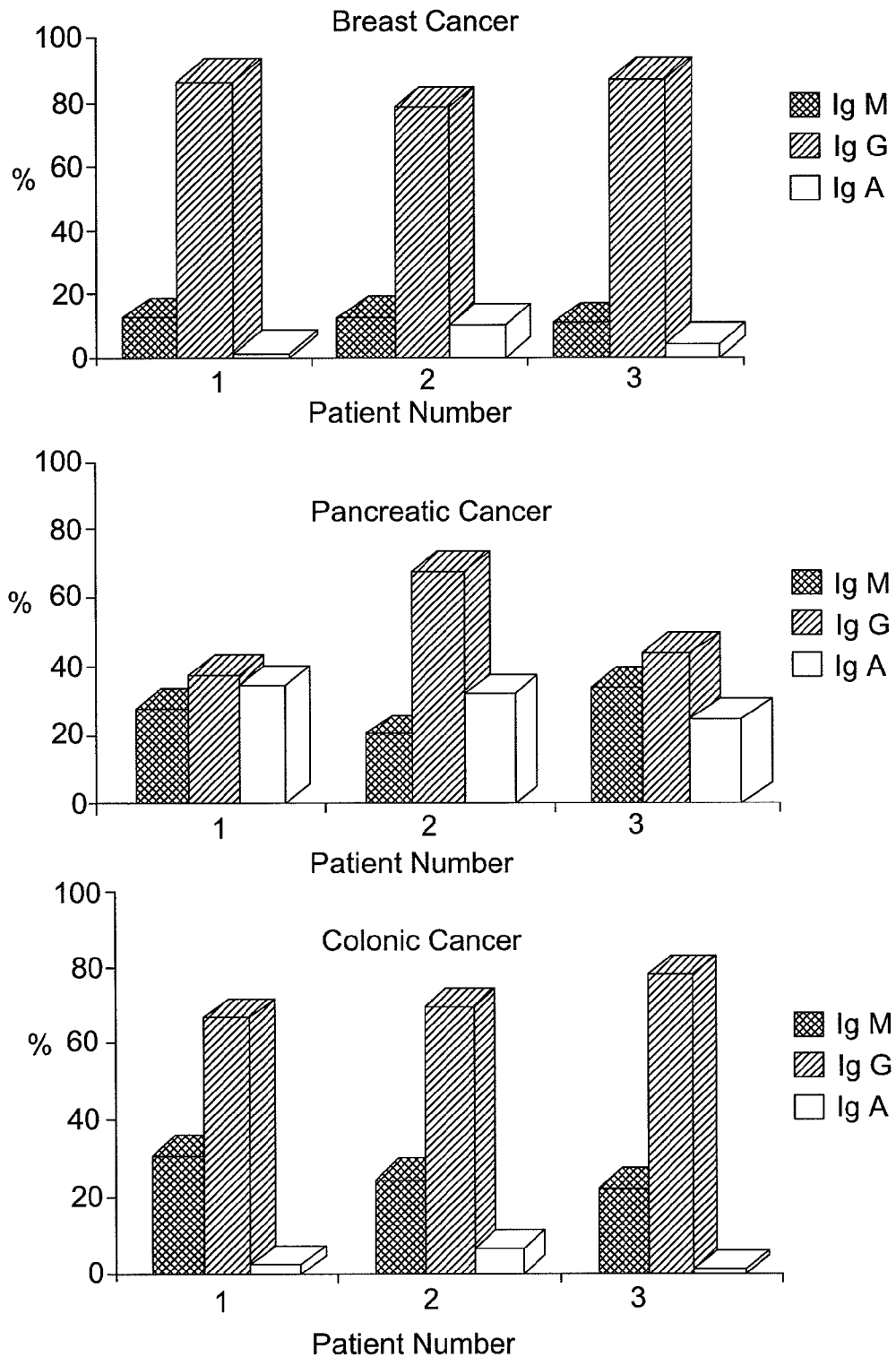
FIG. 13 presents data from experiments revealing the presence of cyclin B1 antibody in the sera of cancer patients.

Moreover, the intermediate and high titers of anti-Cyclin B1 antibody were observed in all three types of cancers (FIG. 12). However the titer of antibody varied depending on the type of cancer (FIG. 13). From breast cancer patients, the predominant isotype was observed to be IgG, while in pancreatic cancer the data suggest that IgA (mucosal immunity) were generated. Colon cancer patients generated predominantly IgG with some IgM.

Example 4

This Example demonstrates that the titer of Cyclin B1 antibody correlates with the presence and recurrence of lung cancer.

Figure 14:
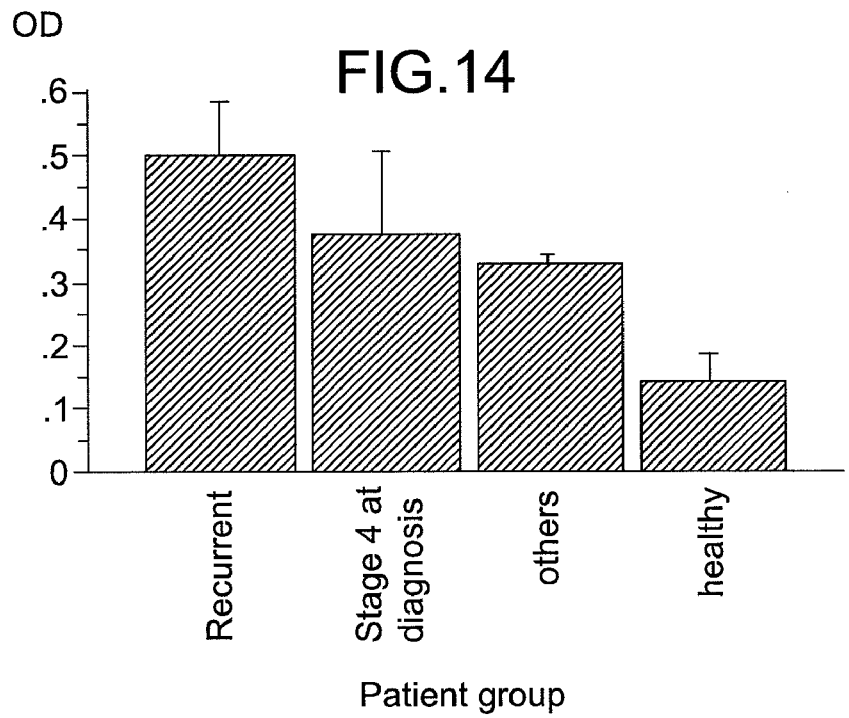
FIG. 14 presents data concerning the expression of cyclin B1 from lung cancer patients and five healthy individuals.
Figure 15:
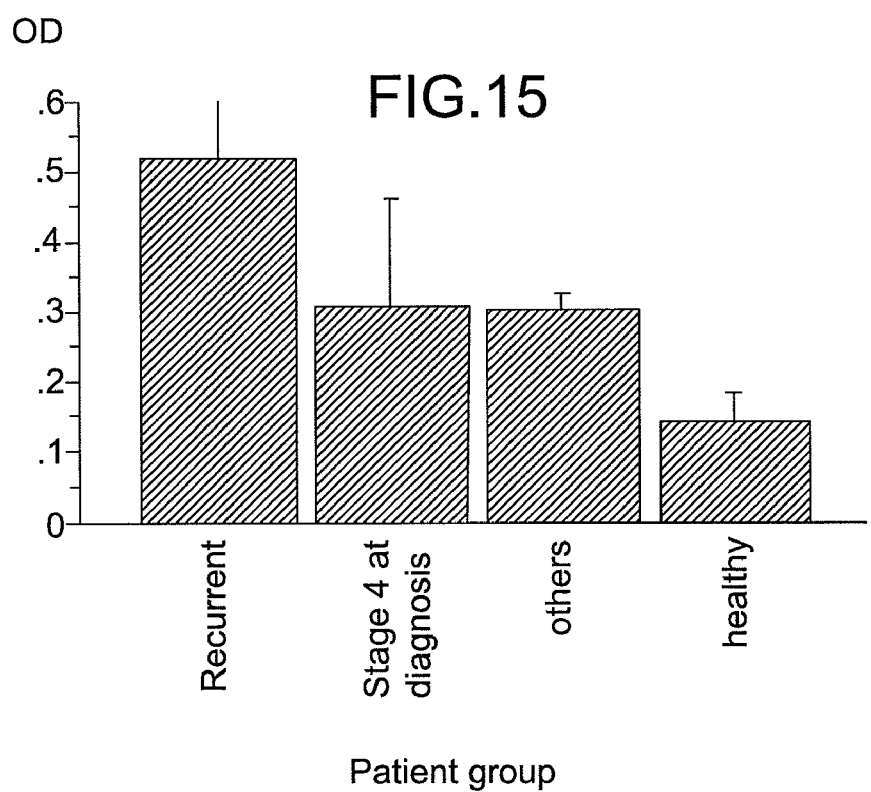
FIG. 15 presents data concerning the expression of cyclin B1 from patients with adinocarcinomas.

Over 100 lung cancer patients were screened as reported in Example 3. Screening lung cancer patients without regard for tumor type revealed that patients with recurrent disease (n=5)

exhibited a higher antibody titer than patients who were stage 4 (n=3) or other stages (n=33) at surgery (FIG. 14). Similar results were observed in patients with lung adenocarcinoma, in that patients with recurrent disease (n=6) exhibited a higher antibody level than patients who were stage 4 (n=4) or other stages (n=60) at surgery (FIG. 15).

These results indicate that assaying for the presence of Cyclin B1 antibodies can server as a diagnostic tool in the detection of tumors and also tumor recurrence.

Example 5

This Example demonstrates that the titer of Cyclin B1 antibody correlates with smoking activity, a known cancer risk.

Figure 16:
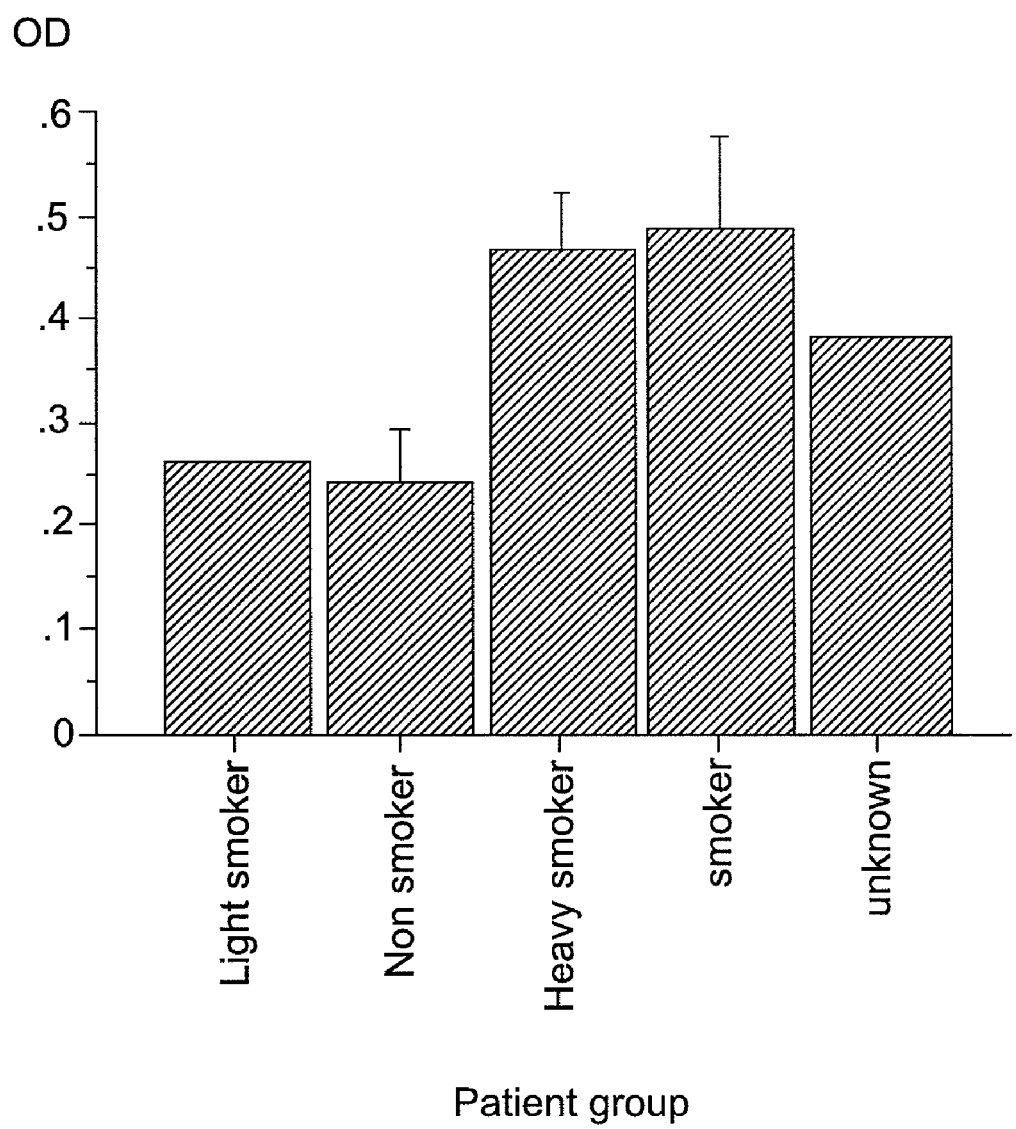
FIG. 16 presents data concerning the expression of cyclin B1 in cigarette smokers and non-smokers.

The titer of Cyclin B1 antibody for light smokers (n=3) was similar to non smokers (n=8) having low or negative antibody titers to cyclin B1. Heavy smokers (n=9) and those identifying themselves as "smokers" smokers (n=4) demonstrated increased antibody titer, and one individual with unknown history exhibited heightened Cyclin B1 antibody titer (see FIG. 16). These results suggest that cyclin B1 may correlate with precancerous development, at least for lung cancer, and may serve as an early diagnostic tool for screening patients at risk of developing cancer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of inducing immune response in a patient comprising introducing a peptide consisting of the amino acid sequence of SEQ ID NO:4 (AGYLMELCC) into a patient under conditions sufficient for the patient to develop an immune response to the peptide.

2. The method of claim 1, wherein the patient is human.

* * * * *

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial
<220> FEATURE:
<223> OTHER INFORMATION: cyclin-derived polypeptide

<400> SEQUENCE: 1

Ala Gly Tyr Leu Met Glu Leu Cys Val
1               5

<210> SEQ ID NO 2
<211> LENGTH: 9
<212> TYPE: PRT
<213> ORGANISM: Artificial
<220> FEATURE:
<223> OTHER INFORMATION: cyclin-derived polypeptide

<400> SEQUENCE: 2

Ala Gly Tyr Leu Met Glu Leu Cys Met
1               5

<210> SEQ ID NO 3
<211> LENGTH: 9
<212> TYPE: PRT
<213> ORGANISM: Artificial
<220> FEATURE:
<223> OTHER INFORMATION: cyclin-derived polypeptide

<400> SEQUENCE: 3
```

```
Ala Gly Tyr Leu Met Glu Leu Cys Phe
1               5
```

<210> SEQ ID NO 4
<211> LENGTH: 9
<212> TYPE: PRT
<213> ORGANISM: Artificial
<220> FEATURE:
<223> OTHER INFORMATION: cyclin-derived polypeptide

<400> SEQUENCE: 4

```
Ala Gly Tyr Leu Met Glu Leu Cys Cys
1               5
```

<210> SEQ ID NO 5
<211> LENGTH: 10
<212> TYPE: PRT
<213> ORGANISM: Artificial
<220> FEATURE:
<223> OTHER INFORMATION: cyclin-derived polypeptide

<400> SEQUENCE: 5

```
Ala Gly Tyr Leu Met Glu Leu Cys Met Ala
1               5                   10
```

<210> SEQ ID NO 6
<211> LENGTH: 10
<212> TYPE: PRT
<213> ORGANISM: Artificial
<220> FEATURE:
<223> OTHER INFORMATION: cyclin-derived polypeptide

<400> SEQUENCE: 6

```
Ala Gly Tyr Leu Met Glu Leu Cys Phe Ala
1               5                   10
```

<210> SEQ ID NO 7
<211> LENGTH: 9
<212> TYPE: PRT
<213> ORGANISM: Artificial
<220> FEATURE:
<223> OTHER INFORMATION: cyclin-derived polypeptide

<400> SEQUENCE: 7

```
Ala Lys Tyr Leu Met Glu Leu Thr Met
1               5
```

<210> SEQ ID NO 8
<211> LENGTH: 10
<212> TYPE: PRT
<213> ORGANISM: Artificial
<220> FEATURE:
<223> OTHER INFORMATION: cyclin-derived polypeptide

<400> SEQUENCE: 8

```
Ala Lys Tyr Leu Met Glu Leu Thr Met Leu
1               5                   10
```

<210> SEQ ID NO 9
<211> LENGTH: 10
<212> TYPE: PRT
<213> ORGANISM: Artificial
<220> FEATURE:
<223> OTHER INFORMATION: Mouse cyclin B1-derived polypeptide

<400> SEQUENCE: 9

```
Ala Lys Tyr Leu Met Glu Leu Ser Met Leu
```

```
1               5              10

<210> SEQ ID NO 10
<211> LENGTH: 10
<212> TYPE: PRT
<213> ORGANISM: Artificial
<220> FEATURE:
<223> OTHER INFORMATION: Rat cyclin B1-derived polypeptide

<400> SEQUENCE: 10

Ala Lys Tyr Leu Met Glu Leu Ser Met Leu
1               5                  10

<210> SEQ ID NO 11
<211> LENGTH: 9
<212> TYPE: PRT
<213> ORGANISM: Artificial
<220> FEATURE:
<223> OTHER INFORMATION: Flu matrix-derived polypeptide

<400> SEQUENCE: 11

Gly Ile Leu Gly Phe Val Phe Thr Leu
1               5

<210> SEQ ID NO 12
<211> LENGTH: 9
<212> TYPE: PRT
<213> ORGANISM: Artificial
<220> FEATURE:
<223> OTHER INFORMATION: HIV-POL-derived polypeptide

<400> SEQUENCE: 12

Ile Leu Lys Glu Pro Gly Ser His Val
1               5
```